US006852738B2

(12) United States Patent
Jones et al.

(10) Patent No.: US 6,852,738 B2
(45) Date of Patent: Feb. 8, 2005

(54) ACYL SULFAMIDES FOR TREATMENT OF OBESITY, DIABETES AND LIPID DISORDERS

(75) Inventors: A. Brian Jones, Clavering (GB); John J. Acton, III, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 6 days.

(21) Appl. No.: 10/470,483

(22) PCT Filed: Jan. 25, 2002

(86) PCT No.: PCT/US02/03119

§ 371 (c)(1),
(2), (4) Date: Jul. 29, 2003

(87) PCT Pub. No.: WO02/060388

PCT Pub. Date: Aug. 8, 2002

(65) Prior Publication Data

US 2004/0073037 A1 Apr. 15, 2004

Related U.S. Application Data

(60) Provisional application No. 60/264,955, filed on Jan. 30, 2001.

(51) Int. Cl.$^7$ .................. A61K 31/16; A61K 31/22; A61K 31/24; A61K 31/27; A61K 31/445
(52) U.S. Cl. .................. 514/330; 514/487; 514/488; 514/489; 514/534; 514/546; 514/595; 514/598; 514/600; 546/227; 560/32; 560/107; 560/163; 560/251; 564/48; 564/47; 564/79
(58) Field of Search .................. 514/330, 487, 514/488, 489, 534, 546, 595, 598, 600; 546/227; 560/32, 107, 163, 251; 564/48, 47, 79

(56) References Cited

U.S. PATENT DOCUMENTS 5,336,690 A * 8/1994 Picard et al. ............... 514/605
6,653,347 B2 * 11/2003 Palovich et al. ............ 514/524

FOREIGN PATENT DOCUMENTS

| WO | WO 93/15047 | 8/1993 |
| WO | WO 97/27852 | 8/1997 |
| WO | WO 00/23457 | 4/2000 |

* cited by examiner

*Primary Examiner*—Peter G. O'Sullivan
(74) *Attorney, Agent, or Firm*—James L. McGinnis; Melvin Winokur

(57) ABSTRACT

A class of acyl sulfamides comprises compounds that are potent ligands for PPAR gamma and generally have antagonist or partial agonist activity. The compounds may be useful in the treatment, control or prevention of obesity, non-insulin dependent diabetes mellitus (NIDDM), hyperglycemia, dyslipidemia, hyperlipidemia, hypercholesterolemia, hypertriglyceridemia, atherosclerosis, vascular restenosis, inflammation, and other PPAR gamma mediated diseases, disorders and conditions.

26 Claims, No Drawings

ACYL SULFAMIDES FOR TREATMENT OF OBESITY, DIABETES AND LIPID DISORDERS

CROSS REFERENCE TO RELATED APPLICATIONS

This application is a U.S. National Phase application under 35 U.S.C. § 371 of PCT Application No. PCT/US02/03119, filed Jan. 25, 2002, and claims priority under 35 U.S.C. § 119 (e) from U.S. application Ser. No. 60/264,955, filed Jan. 30, 2001.

FIELD OF THE INVENTION

The instant invention is concerned with acyl sulfamides and pharmaceutically acceptable salts and prodrugs thereof and their use as therapeutic. compounds, particularly in the treatment of obesity, of Type 2 diabetes mellitus (often referred to as non-insulin dependent diabetes, NIDDM), of conditions that are often associated with these diseases, and of lipid disorders.

BACKGROUND OF THE INVENTION

Excessive weight, and in extreme cases obesity, is a widespread medical problem. This may be due in part to sedentary life styles and poor diet (high in fats and carbohydrates), as well as to a genetic predisposition in many cases.

Pharmaceuticals have been marketed in the past to help control excessive weight and obesity. These have typically tried to achieve weight loss by reducing appetite. Drugs used to reduce appetite have not been universally successful. Many are stimulants and have been abused, and others have had unexpected, and sometimes serious side effects (e.g., fen-phen). An approach that has so far not been exploited successfully is the development of pharmaceuticals that control excessive weight and obesity using a metabolic approach by modulation of receptors that can influence weight gain.

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in high enough insulin concentrations to stimulate the very insulin-resistant tissues. However, dangerously low levels of plasma glucose can result from these last two treatments, and increasing insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia.

Disorders of lipid metabolism or dyslipidemias include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707–714 (1977); Stampfer, et al., N. England J. Med., 325, 373–381 (1991); and Kannel, et al., Ann. Internal Med., 90, 85–91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompanied by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferator activated receptors (PPARs) have attracted considerable scientific attention in the last few years in part because of their emergence as the molecular target of a new group of Type II (non-insulin dependent) diabetes (NIDDM) medicines, the glitazones. Three subtypes of peroxisome proliferator activated receptor (PPAR) have been discovered and described; they are peroxisome proliferator activated receptor gamma (PPARγ), peroxisome proliferator activated receptor alpha (PPARα) and peroxisome proliferator activated receptor delta (PPARδ).

The PPARγ receptor subtypes are involved in activating the program of adipocyte differentiation and are not involved in stimulating peroxisome proliferation in the liver. There are two known protein isoforms of PPARγ: PPARγ1 and PPARγ2 which differ only in that PPARγ2 contains an additional 28 amino acids present at the amino terminus. The DNA sequences for the human isotypes are described in Elbrecht, et al., BBRC 224;431–437 (1996). In mice, PPARγ2 is expressed specifically in fat cells. Tontonoz et al., Cell 79: 1147–1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

It is generally believed that glitazones exert their effects by binding to the peroxisome proliferator activated receptor (PPAR) family of receptors, controlling certain transcription elements having to do with the biological entities listed above. See Hulin et al., Current Pharm. Design (1996) 2, 85–102. A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials have dual PPARα and γ activity. These are expected to improve both insulin sensitivity and the lipid profile in patients having NIDDM. Although glitazones are beneficial in the treatment of NIDDM, there have been some serious adverse events associated with the use of the compounds. The most serious of these has been liver toxicity, which has resulted in a number of deaths. The most serious problems have occurred using troglitazone. Because of the problems that have occurred with the glitazones, researchers in a number of laboratories have been investigating classes of PPAR agonists that are not glitazones and do not contain 1,3-thiazolidinedione moieties. In addition some ligands behave as partial agonists of PPARγ. There are some reasons to believe that such compounds might exhibit modulated pharmacology. As such there has been growing interest in such compounds.

Several patent applications and publications have suggested that PPAR-gamma antagonists or partial agonists may be effective in the treatment of obesity. See WO 96/40128, WO 97/10813, and J. Oberfield, et al., Proc. Nat. Acad. Sci. USA, Vol. 96, pp 6102–6106 (1999). Also, since PPAR-gamma agonists are used in the treatment of NIDDM, and obesity generally accompanies NIDDM, these compounds are generally also claimed as useful in the treatment of obesity.

PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, bezafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia. It is important to note that there may exist a degree of overlap between the functions of PPARγ and PPARα.

The human nuclear receptor gene PPARδ (hPPARδ) has been cloned from a human osteosarcoma cell cDNA library and is fully described in A. Schmidt et al., Molecular Endocrinology, 6:1634–1641 (1992). It should be noted that PPARδ is also referred to in the literature as PPARβ and as NUC1, and each of these names refers to the same receptor; in Schmidt et al. the receptor is referred to as NUC 1. In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity. It has been disclosed in WO97/28149 that agonists of PPARδ are useful in raising HDL plasma levels. WO97/27857, 97/28115, 97/28137 and 97/27847 disclose compounds that are useful as antidiabetic, antiobesity, antiatherosclerosis and antihyperlipidemic agents, and which may exert their effect through activation of PPARs.

SUMMARY OF THE INVENTION

The class of compounds described herein is a new class of PPAR ligands that do not contain a 1,3-thiazolidinedione moiety and therefore are not glitazones. The compounds in this class are primarily PPARγ antagonists or partial agonists. Some of the compounds may also exhibit some level of PPARα agonism. These compounds are useful in the treatment, control and/or prevention of obesity, diabetes, hyperglycemia, insulin resistance, mixed or diabetic dyslipidemia, other lipid disorders, atherosclerosis, vascular restenosis, inflammatory conditions, neoplastic conditions, and other PPARγ mediated diseases, disorders and conditions.

The present invention provides compounds having the structure of Formula I:

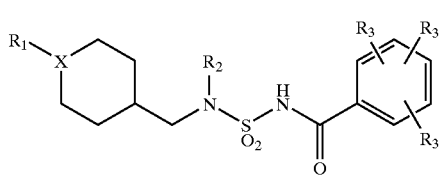

including pharmaceutically acceptable salts and prodrugs thereof, wherein

X is selected from CH and N;

$R_1$ is —$(CH_2)_a(Y_1)_b(Z)_c(Y_2)_d R_4$;

a, b, c, and d are each independently 0 or 1, with the proviso that if c is 0, then b and d are not both 1;

$Y_1$ and $Y_2$ are each independently O or NH;

Z is selected from C(O) and S(O)$_2$;

$R_2$ is selected from H, $C_{1-6}$ alkyl, $C_{2-6}$ alkenyl, $C_{2-6}$ alkynyl, $C_{3-10}$ Cycloalkyl, $C_{6-10}$ Aryl, Heteroaryl, and Heterocycle, and $R_2$ is optionally substituted with 1–5 groups $R_3$;

Each $R_3$ is independently selected from H, halogen, $C_{1-6}$ alkyl, $C_{2-6}$ alkenyl, $C_{2-6}$ alkynyl, $C_{6-10}$ Aryl, —O$C_{1-6}$ alkyl, —O$C_{2-6}$ alkenyl, —O$C_{2-6}$ alkynyl, —O$C_{6-10}$ Aryl, $C_{3-6}$ Cycloalkyl, Heteroaryl, Heterocycle, CN, NO$_2$, S(O)$_m R_4$, SO$_2$NHR$_4$, SO$_2$NR$_4$R$_4$, CO$_2$H, and CONFR$_4$, wherein each alkyl, alkenyl, alkynyl, Aryl, -Oalkyl, -Oalkenyl, -Oalkynyl, -Oaryl, Cycloalkyl, Heteroaryl, and Heterocycle is optionally substituted with 1–5 substituents independently selected from halogen, —OCF$_3$, —OCH$_3$, CF$_3$ and CH$_3$;

Each $R_4$ is independently selected from the group consisting of H, $C_{1-10}$ alkyl, $C_{3-10}$ Cycloalkyl, $C_{2-10}$ alkenyl, $C_{2-10}$ alkynyl, $C_{6-10}$ Aryl, Heterocycle, and Heteroaryl, wherein $R_4$ is optionally substituted with 1–3 groups $R_5$;

Each $R_5$ is independently selected from halogen, $C_{1-6}$ alkyl, $C_{6-10}$ Aryl, —O$C_{1-6}$ alkyl, —O$C_{2-6}$ alkenyl, —O$C_{2-6}$ alkynyl, —O$C_{6-10}$ Aryl, $C_{3-6}$ Cycloalkyl, CN, NO$_2$, CO$_2$H, CO$_2$C$_1$–C$_6$alkyl and CONH$_2$, wherein each alkyl, Aryl, -Oalkyl, -Oalkenyl, -Oalkynyl, -Oaryl, Cycloalkyl and CO$_2$alkyl is optionally substituted with 1–5 substituents independently selected from halogen, —OCF$_3$, —OCH$_3$, CF$_3$ and CH$_3$;

m is 0, 1 or 2;

Each alkyl, alkenyl and alkynyl group may be linear or branched;

Cycloalkyl is a saturated or partly saturated monocyclic or bicyclic carbocyclic ring system;

Aryl is a monocyclic or bicyclic carbocyclic aromatic ring system;

Heterocycle is a fully saturated or partially saturated monocyclic or bicyclic ring system comprising at least one heteroatom selected from N, S and O in the ring and comprising 4 to 11 atoms in the ring; and Heteroaryl is a monocyclic or bicyclic aromatic ring system comprising at least one ring heteroatom selected from N, O and S and comprising 4–11 atoms in the ring or rings.

The compounds are expected to be efficacious in the treatment, control and/or prevention of obesity and non-insulin dependent diabetes mellitus (NIDDM) in humans and in the treatment, control, and/or prevention of hyperlipidemia, dyslipidemia, hypercholesterolemia, hypertrigyceridemia, atherosclerosis, vascular restenosis, inflammatory conditions, neoplastic conditions, and other PPARγ mediated diseases, disorders and conditions. Many of these latter conditions listed above (hyperlipidemia, dyslipidemia, etc.) are often associated with NIDDM, but may also occur independently of NIDDM.

DETAILED DESCRIPTION OF THE INVENTION

The invention has numerous embodiments. Several subsets of compounds are described below.

One group of compounds comprises compounds having formula I in which X is CH.

A preferred subset of the above group of compounds in which X is CH comprises compounds in which $R_1$ is selected from CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, CH$_2$NHS(O)$_2$R$_4$, CONHR$_4$, S(O)$_2$NHR$_4$, OCONHR$_4$, NHCOOR$_4$, NHCONHR$_4$, NHS(O)$_2$NHR$_4$, NHCOR$_4$, and NHS(O)$_2$R$_4$.

A preferred subgroup of the above subset of compounds includes compounds in which $R_1$ is CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, or CH$_2$NHS(O)$_2$R$_4$.

Another group of compounds comprises those compounds having Formula I in which X is N. A preferred subgroup comprises compounds in which $R_1$ is selected from CONHR$_4$, COOR$_4$, COR$_4$, S(O)$_2$R$_4$, and S(O)$_2$NHR$_4$.

Preferred embodiments also include compounds in which $R_2$ is selected from $C_{1-6}$ alkyl, CH$_2$C$_{3-10}$ Cycloalkyl and CH$_2$C$_{6-10}$ Aryl, wherein $R_2$ is optionally substituted with 1–3 halogens, and Cycloalkyl and Aryl are optionally substituted with 1–3 groups $R_3$. Preferred compounds from these embodiments include compounds in which $R_2$ is CH$_2$phenyl, where phenyl is optionally substituted with 1–3 groups $R_3$.

Another preferred embodiment includes compounds in which each $R_3$ is independently selected from the group consisting of H, halogen, $C_{1-6}$ alkyl, and —O$C_{1-6}$ alkyl, wherein alkyl and -Oalkyl are optionally substituted with 1–5 fluorine atoms.

Another preferred embodiment includes compounds having Formula I in which each $R_4$ is independently selected from the group consisting of H, $C_{1-6}$ alkyl, $C_{3-6}$ Cycloalkyl, phenyl, and Heteroaryl, wherein Cycloalkyl is a monocyclic carbocyclic ring and Heteroaryl is a monocyclic 5 or 6-membered aromatic ring having at least one heteroatom selected from O, S and N in the ring, and $R_4$ is optionally substituted with 1–3 $R_5$. In highly preferred compounds having Formula I, $R_4$ is selected from the group consisting of H, phenyl and $C_{1-6}$alkyl, where phenyl is optionally substituted with 1–3 groups independently selected from halogen, CH$_3$, CF$_3$, —OCH$_3$ and —OCF$_3$, and alkyl is optionally substituted with 1–3 halogens and/or one phenyl, which is optionally substituted with 1–3 groups independently selected from halogen, CH$_3$, CF$_3$, —OCH$_3$ and —OCF$_3$.

A preferred group comprises compounds in which:

when X is CH, $R_1$ is selected from CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, and CH$_2$NHS(O)$_2$R$_4$, and when X is N, $R_1$ is selected from $CONHR_4$, $COOR_4$, $COR_4$, $S(O)_2R_4$, and $S(O)_2NHR_4$. In these groups, regardless of whether X is CH or N:

$R_2$ is benzyl or $C_{1-6}$ alkyl, and $R_2$ is optionally substituted with 1–3 $R_3$;

$R_3$ is selected from H, halogen, $C_{1-6}$alkyl, —$OCH_3$ and —$OCF_3$, wherein alkyl is optionally substituted with 1–3 halogens; and Each $R_4$ is independently selected from H, phenyl and $C_{1-6}$alkyl, wherein phenyl is optionally substituted with 1–3 groups independently selected from halogen, $CH_3$, $CF_3$, —$OCH_3$ and —$OCF_3$, and alkyl is optionally substituted with 1–3 halogens and/or 1 phenyl, which is optionally substituted with 1–3 groups independently selected from halogen, $CH_3$, $CF_3$, —$OCH_3$ and —$OCF_3$.

Particularly preferred groups of compounds include those compounds having Formula I in which $R_2$ is benzyl.

The compounds of Formula I can have up to 3 substituents $R_3$ on the benzamide ring. More typically, there are 1–2 groups R3 on the benzamide ring.

Specific examples of compounds of this invention, which also include pharmaceutically acceptable salts and prodrugs, are provided as Examples 1–20, named below:

1. (4-{[benzyl({[3,5-bis(trifluoromethyl)benzoyl] amino}sulfonyl)amino]methyl}cyclohexyl)methyl benzoate;
2. (4-{[benzyl({[3,5-bis(trifluoromethyl)benzoyl] amino}sulfonyl)amino]methyl}cyclohexyl)methyl pentanoate;
3. (4-{[benzyl({[3,5-bis(trifluoromethyl)benzoyl] amino}sulfonyl)amino]methyl}cyclohexyl)methyl phenylcarbamate;
4. (4-{[({[3,5-bis(trifluoromethyl)benzoyl]amino}sulfonyl) amino]methyl}cyclohexyl)methyl phenylcarbamate;
5. (4-{[benzyl({[3,5-bis(trifluoromethyl)benzoyl] amino}sulfonyl)amino]methyl}cyclohexyl)methyl benzylcarbamate;
6. (4-{[benzyl({[3,5-bis(trifluoromethyl)benzoyl] amino}sulfonyl)amino]methyl}cyclohexyl)methyl 2-phenylethycarbamate
7. (4-{[benzyl({[3,5-bis(trifluoromethyl)benzoyl] amino}sulfonyl)amino]methyl}cyclohexy)methyl 3-methoxyphenylcarbamate;
8. (4-{[benzyl({[3,5-bis(trifluoromethyl)benzoyl] amino}sulfonyl)amino]methyl}cyclohexyl)methyl butyl-carbamate;
9. (4-{[benzyl({[3,5-bis(trifluoromethyl)benzoyl] amino}sulfonyl)amino]methyl}cyclohexyl)methyl 1-methylbutylcarbamate;
10. N-benzyl-N'-[3,5-bis(trifluoromethyl)benzoyl]-N-({4-[(pentyloxy)methyl]cyclohexyl}methyl)sulfamide;
11. N-benzyl-4-{[benzyl({[3,5-bis(trifluoromethyl)benzoyl] amino}-sulfonyl)amino]methyl}cyclohexane carboxamide;
12. N-[(4-{[benzyl({[3,5-bis(trifluoromethyl)benzoyl] amino}sulfonyl)amino]methyl}cyclohexyl)methyl]-N'-phenylurea;
13. N-[(4-{[benzyl({[3,5-bis(trifluoromethyl)benzoyl] amino}sulfonyl)amino]methyl}cyclohexyl)methyl] pentanamide;
14. N-[(4-{[benzyl({[3,5-bis(trifluoromethyl)benzoyl] amino}sulfonyl)amino]methyl}cyclohexyl)methyl] benzamide;
15. N-[(4-{[benzyl({[3,5-bis(trifluoromethyl)benzoyl] amino}sulfonyl)amino]methyl}cyclohexyl)methyl]-N'-butylurea;
16. Butyl (4-{[benzyl({[3,5-bis(trifluoromethyl)benzoyl] amino}sulfonyl)amino]methyl}cyclohexyl)methyl car-bamate;
17. N-[(4-{[benzyl({[3,5-bis(trifluoromethyl)benzoyl] amino}sulfonyl)amino]methyl}cyclohexyl)methyl] benzenesulfonamide;
18. (4-{[({[3,5-bis(trifluoromethyl)benzoyl] amino}sulfonyl)(ethyl)amino]methyl}cyclohexyl)methyl phenylcarbamate;
19. {4-[(benzyl{[(3,5-dimethylbenzoyl)amino] sulfonyl}amino)methyl]cyclohexyl}methyl phenylcar-bamate; and
20. 4-(benzyl-{[(4-t-butylbenzoyl)amino] sulfonyl}aminomethyl)-1-piperidinecarboxylic acid phe-nylmethyl ester.

The structures of specific compounds are shown in the following Table of Examples. Pharmaceutically acceptable salts and prodrugs are also included:

| EXAMPLE No. | STRUCTURE |
| --- | --- |
| 1 | 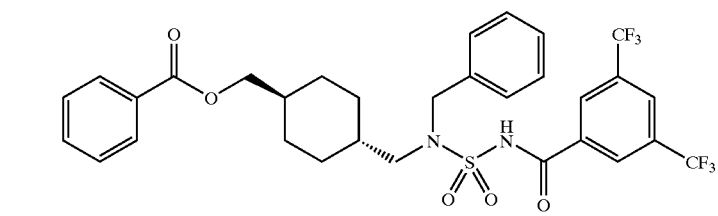 |
| 2 | 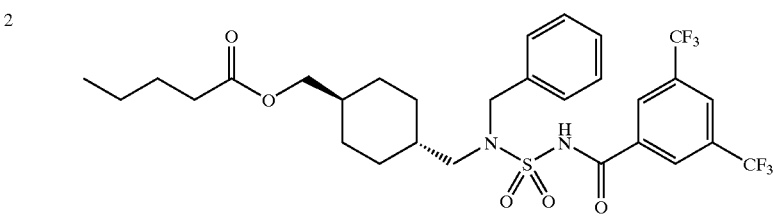 |

-continued
| EXAMPLE No. | STRUCTURE |
|---|---|
| 3 | 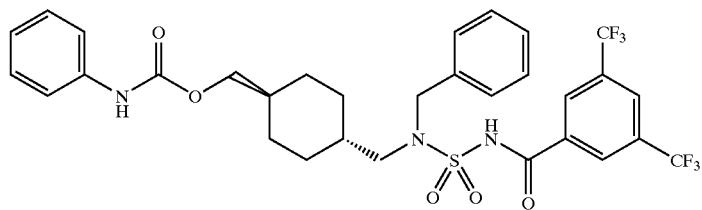 |
| 4 | 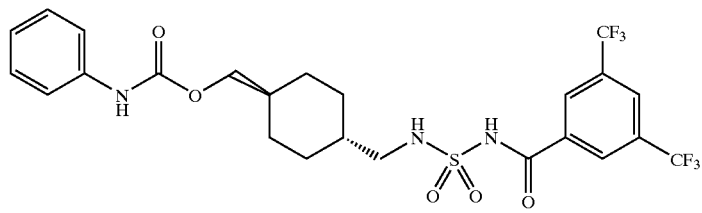 |
| 5 | 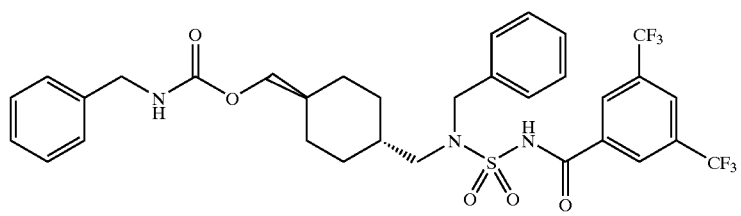 |
| 6 | 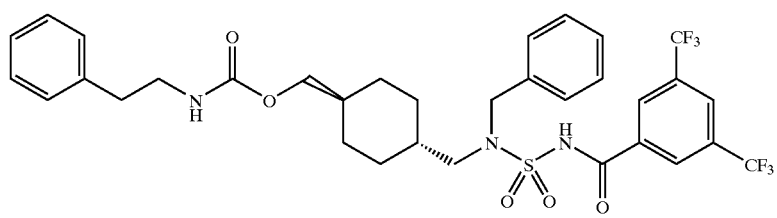 |
| 7 | 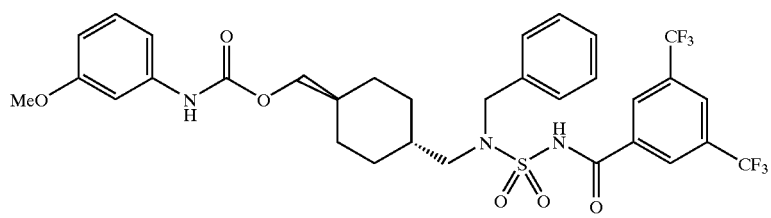 |
| 8 | 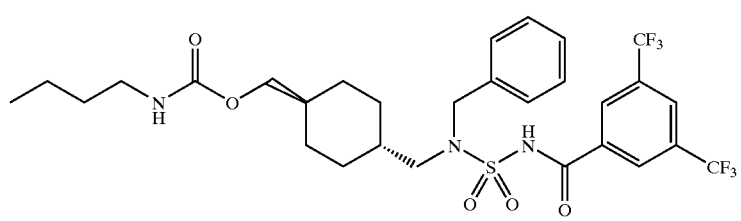 |
| 9 | 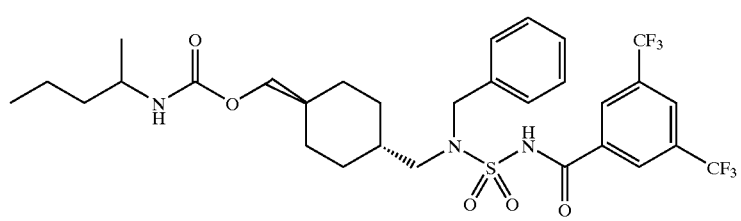 |

-continued
| EXAMPLE No. | STRUCTURE |
|---|---|
| 10 | 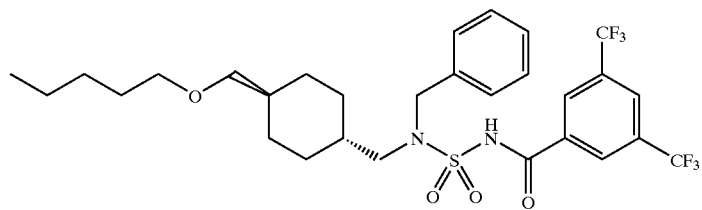 |
| 11 | 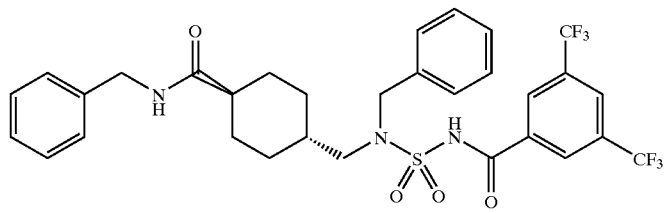 |
| 12 | 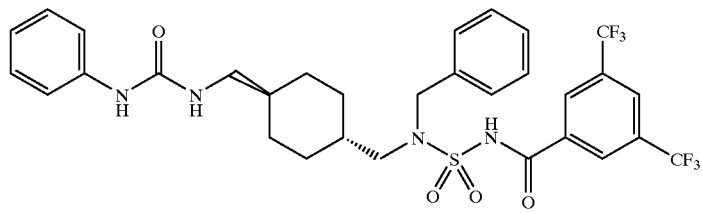 |
| 13 | 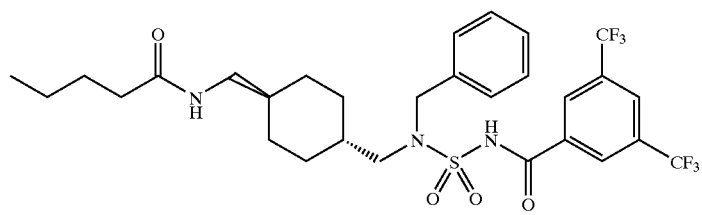 |
| 14 | 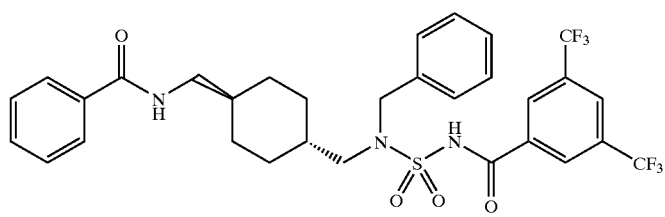 |
| 15 | 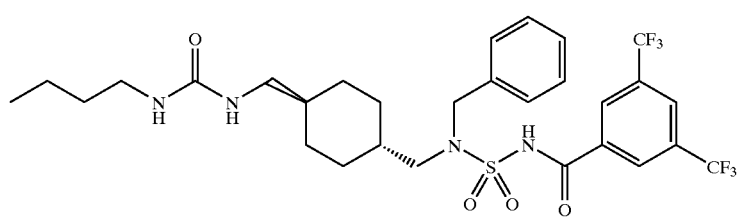 |
| 16 | 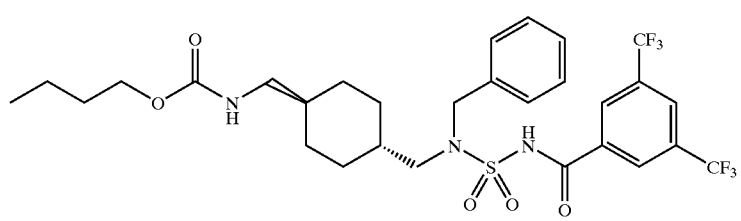 |

| EXAMPLE No. | STRUCTURE |
|---|---|
| 17 | 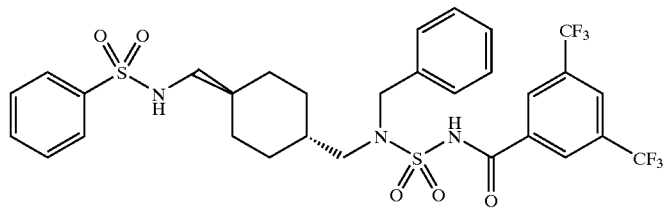 |
| 18 | 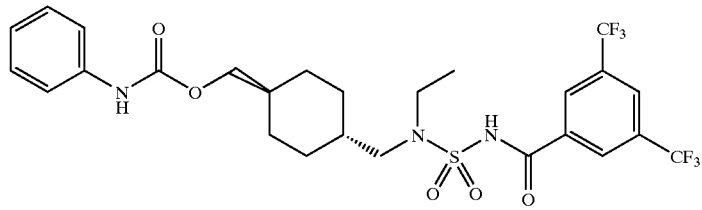 |
| 19 | 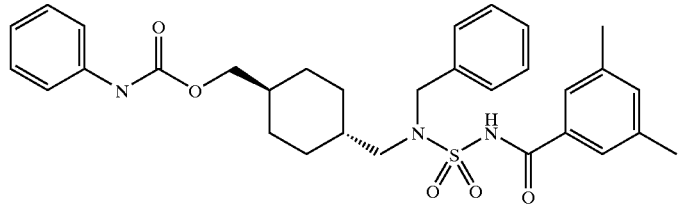 |
| 20 | 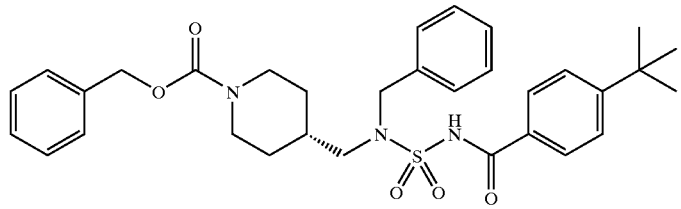 |

The invention further includes pharmaceutical compositions comprising any of the compounds of formula I as described above, and any of the specific compounds exemplified herein, and a pharmaceutically acceptable carrier.

The compounds as defined above are useful in the following methods of treating, controlling, and preventing diseases, and may also have utility in treating certain other diseases and conditions that are not listed below.

(1) a method for treating, controlling, or preventing obesity in a mammalian patient in need of such treatment which comprises administering to the patient a therapeutically effective amount of a compound of Formula I;

(2) a method for treating, controlling or preventing diabetes mellitus, and particularly non-insulin dependent diabetes mellitus, in a mammalian patient in need of such treatment which comprises administering to the patient a therapeutically effective amount of a compound of Formula I;

(3) a method for treating, controlling, or preventing hyperglycemia in a mammalian patient in need of such treatment which comprises administering to the patient a therapeutically effective amount of a compound of Formula I;

(4) a method for treating, controlling, or preventing lipid disorders, hyperlipidemia, or low HDL in a mammalian patient in need of such treatment which comprises administering to the patient a therapeutically effective amount of a compound of Formula I;

(5) a method for treating, controlling, or preventing hypercholesterolemia in a mammalian patient in need of such treatment which comprises administering to the patient a therapeutically effective amount of a compound of Formula I;

(6) a method for treating, controlling, or preventing hypertriglyceridemia in a mammalian patient in need of such treatment which comprises administering to the patient a therapeutically effective amount of a compound of Formula I;

(7) a method for treating, controlling, or preventing dyslipidemia, including low HDL cholesterol, in a mammalian patient in need of such treatment which comprises administering to the patient a therapeutically effective amount of a compound of Formula I;

(8) a method for treating, controlling, or preventing atherosclerosis in a mammalian patient in need of such treatment which comprises administering to the patient a therapeutically effective amount of a compound of Formula I. It is understood that the sequellae of atherosclerosis (angina, claudication, heart attack, stroke, etc.) are thereby treated.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated or partly saturated monocyclic or bicyclic carbocyclic ring system having from 3 to 12 carbon atoms, unless otherwise defined. The term also can include a monocyclic ring fused to an aryl group or other ring system. Examples of cycloalkyl include cyclopropyl, cyclobutyl, cyclopentyl, cyclohexyl, cyclohexenyl, cycloheptyl, and the like.

"Aryl" (and "arylene") means mono-or bicyclic aromatic rings containing only carbon ring atoms. Aryl groups that are described herein are 6-10-membered monocyclic or bicyclic ring systems, unless otherwise defined, and are preferably phenyl or naphthyl. Phenyl is most preferred. The term "aryl" also may describe a phenyl group that is fused to a monocyclic cycloalkyl or monocyclic heterocyclic group. "Heterocycle" and "heterocyclic" means a fully or partially saturated monocyclic or bicyclic ring system containing at least one heteroatom selected from N, S and O in the ring, where the ring system has 4 to 11 atoms, except where defined otherwise. S may also have 1–2 O atoms bound to it that are not in the ring itself. Examples of aryl substituents include phenyl and naphthyl. Fused aryls include the phenyl ring of indanyl, indenyl, and tetrahydronaphthyl. Examples of aryl fused to heterocyclic groups include 2,3-dihydrobenzofuranyl, dihydrobenzopyranyl, and the like. Examples of heterocycles include tetrahydrofuran, piperazine, tetrahydropyran, and morpholine.

"Heteroaryl" (and heteroarylene) means a mono-or bicyclic aromatic ring system containing 4–11 atoms in the ring or rings, including at least one ring heteroatom selected from N, O and S in the ring or rings (including SO and $SO_2$, where the O atoms are not in the ring. Heteroaryl as a substituent also includes bicyclic aromatic rings having a heteroaromatic ring fused to a carbocyclic aromatic ring, such as benzene. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

In the description above and elsewhere, including the claims, when something is described as being "optional," such as one or more substituents or compounds from one or more lists of optional substituents or compounds, one of the options is that the substituent or compound may be absent.

Optical Isomers—Diastereomers—Geometric Isomers—Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

In compounds of Formula I in which X is CH, the groups that are in the 1,4-positions of the cyclohexyl ring can be cis or trans relative to each other. Both cis and trans isomers are included in the compounds defined by Formula I. The trans compounds are believed to be more active and are preferred.

Some of the compounds described herein may contain olefinic double bonds, and unless specified otherwise, are meant to include both E and Z geometric isomers.

Some of the compounds described herein may exist with different points of attachment of hydrogen accompanied by one or more double bond shifts, referred to as tautomers. For example, a ketone and its enol form are keto-enol tautomers. The individual tautomers as well as mixtures thereof are encompassed with compounds of Formula I.

If desired, racemic mixtures of compounds of Formula I may be separated by the coupling of a racemic mixture of the compounds of Formula I to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds of Formula I can also be separated directly by chromatographic methods utilizing chiral stationary phases, which methods are well known in the art.

Alternatively, any enantiomer of a compound of the general Formula I may be obtained by stereoselective synthesis using optically pure starting materials or reagents of known configuration. Such methods are well known in the art.

Compounds of Formula I that have more than one asymmetric center and that occur as mixtures of diastereomers can similarly be separated into single diastereomers by standard methods, and these can be further separated to individual enantiomers as described above.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Metabolites of the compounds of this invention that are therapeutically active and that have the structure shown in formula I also are within the scope of the claimed parent compounds. Prodrugs, which are compounds that are converted to the claimed compounds as they are being administered to a patient or after they have been administered to a patient, are also within the scope of the claimed active compounds.

Utilities

Compounds of the present invention are antagonists or partial agonists of PPARγ. Compounds of the present invention are useful in treating, controlling or preventing diseases, disorders or conditions, wherein the treatment is mediated by the modulation of PPAR γ. One aspect of the present invention provides a method for the treatment, control or prevention of such diseases, disorders, or conditions in a mammal which comprises administering to such mammal a therapeutically effective amount of a compound of Formula I. The compounds are particularly useful for the treatment of obesity and/or non-insulin dependent diabetes mellitus. This is discussed in detail in WO01/30343, which is incorporated by reference into this patent application in its entirety. The diseases, disorders or conditions for which compounds of the present invention are generally useful in treating, controlling or preventing include, but are not limited to, (1) obesity, (2) diabetes mellitus, and especially non-insulin dependent diabetes mellitus (NIDDM), (3) hyperglycemia, (4) low glucose tolerance, (5) insulin resistance, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflamatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30) other skin diseases and dermatological conditions modulated by PPAR, (31) high blood pressure, (32) Syndrome X, (33) ovarian hyperandrogenism (polycystic ovarian syndrome), and other disorders where insulin resistance is a component.

Another aspect of the invention provides a method of treating cachexia. PPARα is known to be necessary for an appropriate energy sparing response to starvation, and inappropriate metabolism and energy utilization is clearly responsible for the wasting of cachexia.

Another aspect of the invention provides a method of treating a variety of skin diseases and dermatological conditions that are modulated by PPARα and/or γ agonists. These diseases and conditions include psoriasis and acne vulgaris. Examples of other skin diseases and dermatological disorders that may be treated include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts inluding verruca, condyloma, or condyloma accuminatum, and human papilloma viral (HPV) infections such as venereal warts, viral warts, molluscum contagiosum, leukoplakia, lichen planus; keratitis, skin cancer such as basal cell carcinoma and cutaneous T cell lymphoma, and localized benign epidermal tumors (keratoderma, epidermal naevi).

Another aspect of the invention provides a method of treating inflammatory conditions, including inflammatory bowel disease, Crohn's disease, and ulcerative colitis by administering an effective amount of a PPAR agonist. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing obesity, diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment, prevention, suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, pravastatin, fluvastatin, atorvastatin, rivastatin, itavastatin, ZD-4522 and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as for example beta-sitosterol, (vii) acyl CoA:cholesterol acyltransferase inhibitors, such as for example avasimibe, and (viii) anti-oxidants, such as probucol;

(f) PPARδ agonists such as those disclosed in WO97/28149;

(g) antiobesity compounds such as fenfluramine, dexfenfluramine, phentiramine, sulbitramine, orlistat, neuropeptide Y5 inhibitors, and $\beta_3$ adrenergic receptor agonists;

(h) an ileal bile acid transporter inhibitor; and (i) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$]AD5075, (21 Ci/mmole), ±test compound as described in Berger et al., Novel peroxisome proliferator-activated receptor (PPARγ) and PPARδ ligands produce distinct biological effects, J. Biol. Chem. (1999), 274, 6718–6725.) Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$] 3-chloro-4-(3-(7-propyl-3-trifluoromethyl-6-benz-[4,5]-isoxazoloxy)propylthio)phenylacetic acid (17 Ci/mmole), ±test compound as described in Berger et al., Novel peroxisome proliferator-activated receptor (PPARγ) and PPARδ ligands produce distinct biological effects, J. Biol. Chem. (1999), 274, 6718–6725). [$^3$H$_2$] 3-chloro-4-(3-(7-propyl-3-trifluoromethyl-6-benz-[4,5-isoxazoloxy)propylthio) phenylacetic acid as a non-labelled compound is taught in Ex. 20 of WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$](3-(4-(3-phenyl-7-propyl-6-benz-[4,5]-isoxazoloxy)butyloxy))phenylacetic acid (34 Ci/mmole), ±test compound. This is a tritium labelled variant of Ex.62 in WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at $12 \times 10^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37 ° C. in a humidified atmosphere of 10% $CO_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% $CO_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Measurement of Antagonism/Partial Agonism

Antagonists and partial agonists are well known in the art. The above assays can be used to measure the PPARγ antagonism/partial agonism of the compounds disclosed herein or of other compounds by measuring the PPARγ agonism of a "full" agonist and then measuring the inhibition (usually as a % inhibition) of the full PPARγ agonist when a sample of the compound being tested is also included in the assay. A full agonist is a PPARγ agonist that is known to be very effective in comparison with other PPARγ agonists. Examples of full agonists include rosiglitazone, pioglitazone and 3-chloro-4-(3-(3-phenyl-7-propylbenzofuran-6-yloxy)propylthio)phenylacetic acid (described by Berger et al, Journal of Biological Chemistry Vol 274, 6718–6725, 1999). The synthesis of 3-chloro-4-(3-(3-phenyl-7-propylbenzofuran-6-yloxy)propylthio)phenylacetic acid is disclosed in U.S. Pat. No. 5,859,051.

Compounds that are PPARγ antagonists or partial agonists and that may be useful in treating obesity and possibly other conditions that are modulated by PPARγ are expected to inhibit the PPARγ agonism of a full PPARγ agonist to a level of less than 50% of its normal level of agonism using the GAL4 chimeric receptor transcriptional assay, and possibly less than 25% of its normal level of agonism.

A second assay method that can also be used is the PPAR-CBP HTRF assay, described by Zhou, et al, *Molecular Endocrinology*, Vol. 12, 1594–1604 (1998), which reference is incorporated herein by reference. A third assay method that can be used is the 3T3-L1 pre-adipocyte differentiation assay, described by Berger et al, *Journal of Biological Chemistry*, Vol 274, 6718–6725 (1999). These assays are summarized below.

PPAR-CBP HTRF Assay

Briefly, 100 mM HEPES, 123 mM KF, 0.125% (wt/vol) CHAPS, 0.05% dry milk, 1 nM GST-PPARγLBD, 2 nM anti-GST-(Eu)K, 10 nM biotin-CBP$_{1-453}$, 20 nM SA/XL665, a potent PPARγ agonist, and the compound being tested (100 nM) at several concentrations are incubated overnight at 4° C. Fluorescence is then read on a Discovery instrument (Packard). Data are expressed as the ratio, multiplied by a factor of $10^4$, of the emission intensity at 665 nM to that at 620 nM.

3T3-L1 Preadipocyte Differentiation Assay

3T3-L1 cells are obtained from American Type Culture Collection. Passage numbers 3 to 9 are used. Monolayer fibroblasts are maintained in medium A (Dulbecco's modified Eagle's medium with 10% fetal calf serum, 100 units/ml penicillin, and 100 μg/ml streptomycin) at 37° C. in 5% $CO_2$. For experiments, the cells are incubated with medium A (supplemented with 150 nM insulin, 1 μM dexamethasone) in the presence of 100 nM rosiglitazone and various concentrations of test compound for 5 days (with one medium change). Total RNA is prepared using Ultraspec™ RNA isolation system (Biotecx, Houston, Tex.). RNA concentration is quantitated by absorbance at 260 nm. Equal amounts of RNA samples are denatured in formamide/formaldehyde and applied to Hybond™-N membranes (Amersham) using a slot blot apparatus (BioRad). Prehybridization is performed at 42° C. for 1–3 h in 40–50% formamide in a solution containing 25 mM sodium phosphate, pH 7.4, 0.9 M sodium chloride, 50 mM sodium citrate, 0.1% each of gelatin, ficoll, and polyvinylpyrollidone, 0.5% SDS, and 100 μg/ml denatured salmon sperm DNA. Hybridization is carried out at the same temperature for 20 h in the same solution with $^{32}$P-labeled aP2 cDNA probe ($2 \times 10^6$ cpm/ml). After washing the membranes under appropriately stringent conditions, the hybridization signals are analyzed with a PhosphorImager (Molecular Dynamics).

SYNTHETIC METHODS AND EXAMPLES

The following Examples are provided to illustrate the invention, including methods of making the compounds of the invention, and are not to be construed as limiting the invention in any manner. The meanings of the substituent groups X, Y, Z, R and $R_1$ in the following schemes can be determined by comparison of the schemes with Examples 1–20.

General Scheme 1

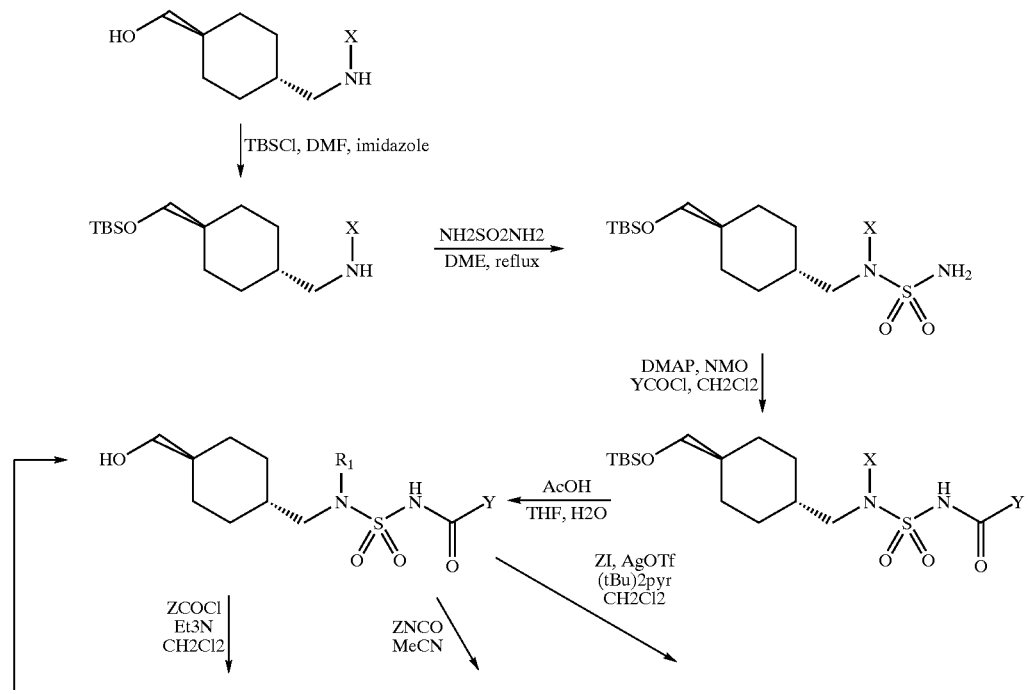

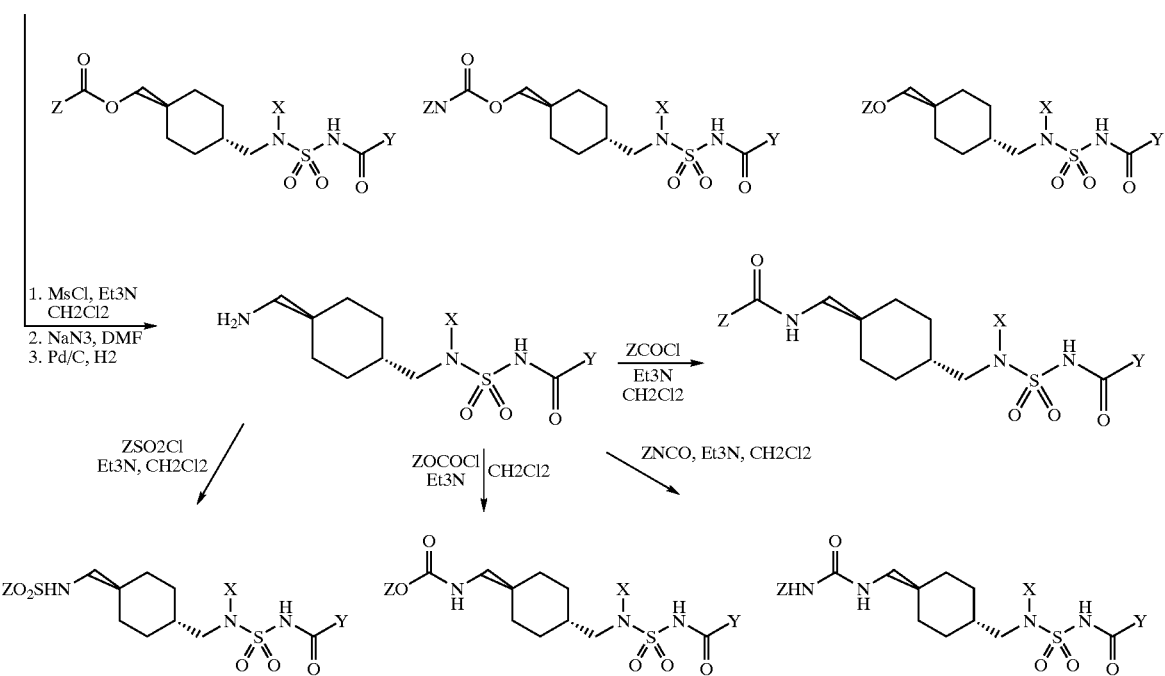
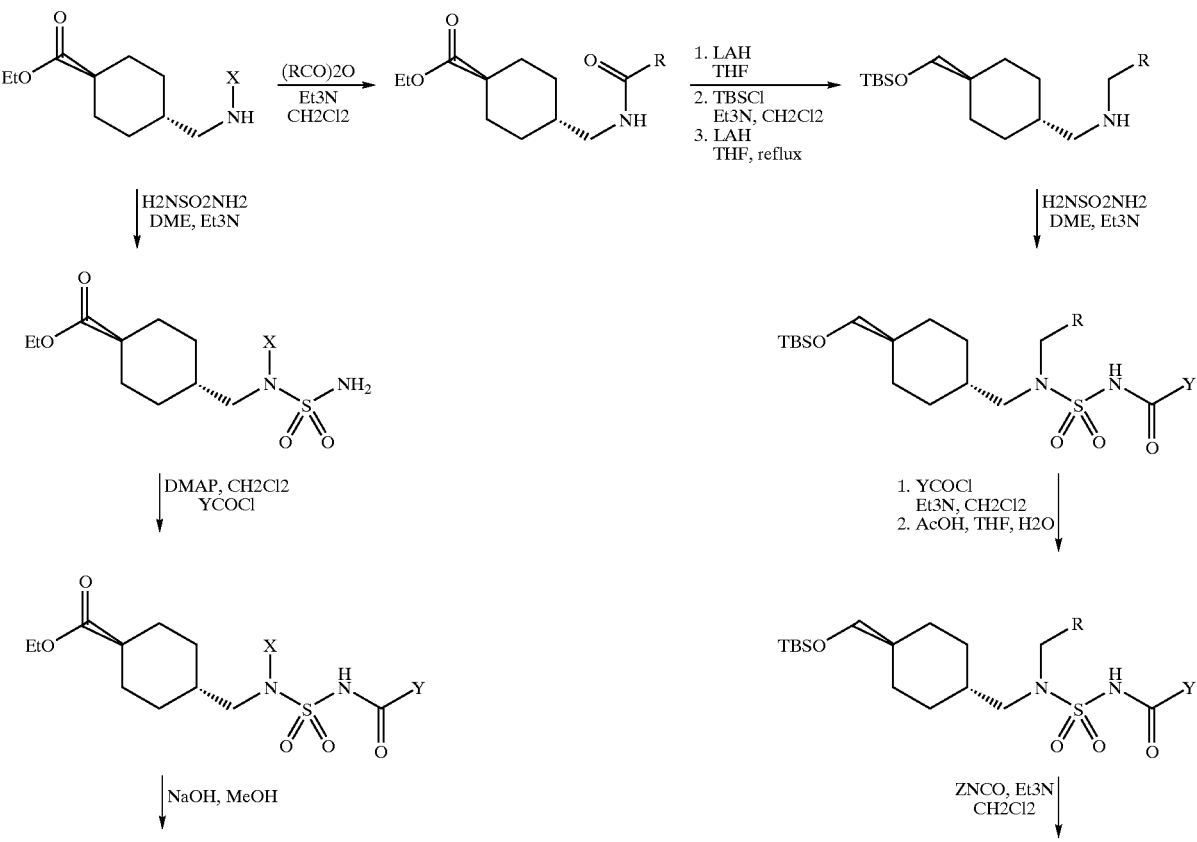
General Scheme 2

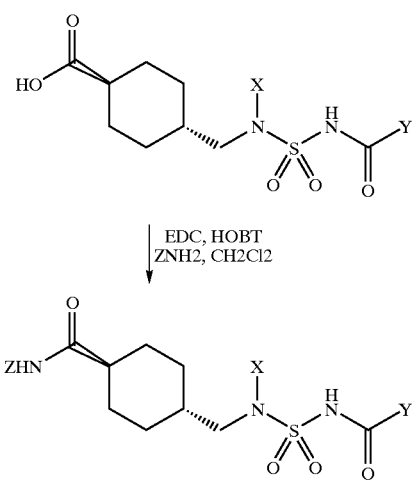

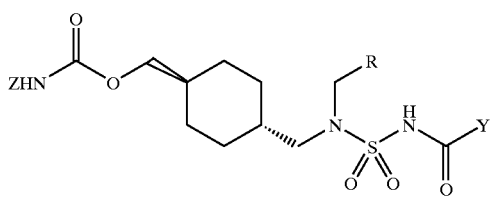

General Scheme 3

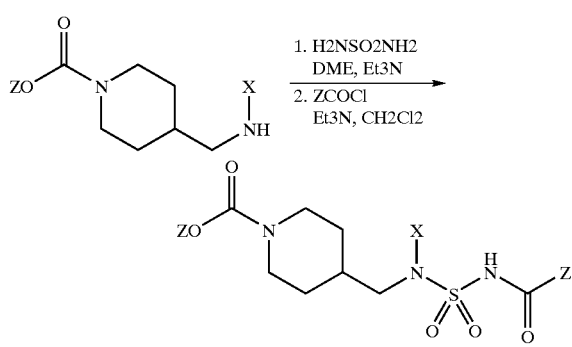

EXAMPLES

Example 1

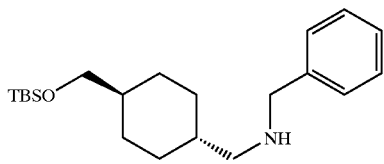
(1)

N-benzyl-N-{[4-({[tert-butyl(dimethyl)silyl]oxy}methyl) cyclohexyl]methyl}amine (1): {4-[(benzylamino)methyl] cyclohexyl}methanol (CAS 46843-17-8) (594 mg, 2.55 mmole, 1.0 eq) was dissolved in 2 mL of N,N-dimethylfornamide, then treated with imidazole (434 mg, 6.1 mmole, 2.5 eq) and dimethyl-tert-butylsilyl chloride (461 mg, 3.06 mmole, 1.2 eq). The solution was stirred for 18 hours, then it was diluted with dichloromethane and washed 3× with water. The organic was dried over potassium carbonate, filtered and evaporated. The crude isolate was purified by silica gel chromatography to give the TBS protected alcohol (1) in quantitative yield. Mass spectrum (ES+), calculated M+347.26, observed (M+1) 348.3.

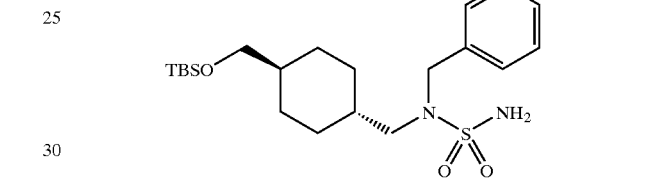
(2)

N-benzyl-N-{[4-({[tert -butyl(dimethyl)silyl]oxy}methyl) cyclohexyl]methyl}sulfamide (2): (1)(880 mg, 2.53 mmole, 1.0 eq) was dissolved in 20 mL of 1,2-dimethoxyethane. Sulfamide (1.22 grams, 12.66 mmole, 5.0 eq) was added and the reaction was stirred at reflux overnight. Monitoring by TLC shows that the reaction is complete, so the 1,2-dimethoxyethane was evaporated and the crude reconstituted in dichloromethane. The organic layer was washed with water, dried, filtered and evaporated to give the target compound in 88% yield. Mass spectrum (ES+), calculated M+426.69, observed (M+1) 427.3.

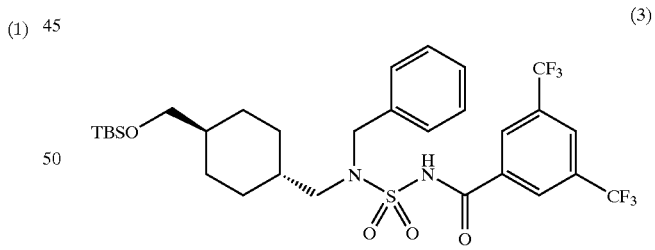
(3)

N-benzyl-N'-[3,5-bis(trifluoromethyl)benzoyl]-N-{[4-({ [tert -butyl(dimethyl)silyl]oxy}methyl) cyclohexyl] methyl}sulfamide (3): Intermediate 2 (914 mg, 2.14 mmole, 1.0 eq) was dissolved in 30 mL of dichloromethane, and dimethylaminopyridine (288 mg, 2.36 mmole, 1.1 eq), N-methylmorpholine (0.26 mL, 2.36 mmole, 1.1 eq), and 3,5-bis(trifluoromethyl)benzoyl chloride (0.39 mL, 2.14 mmole, 1.0 eq) was stirred at room temperature for 24 hours. The reaction mixture was then diluted with dichloromethane, washed with 1N hydrochloric acid, dried over sodium sulfate, filtered and evaporated. Crude was dissolved in petroleum ether, product precipitates out cleanly. Yield of target compound 50%. NMR 300 Mz δ 0.0

(S, 6H), 0.87 (s, 9H), 0–68–1.0 (m, 4H), 1.23–1.55 (m, 2H), 1.76 (Br d, 4H, J=12 Hz), 3.35 (d, 2H, J=7.5 Hz), 3.42 (d, 2H, J=7.5 Hz), 4.58 (s, 2H), 7.13–7.39 (mult, 6H), 8.09 (d, 1H, J=8.5 Hz), 8.10 (s, 1H), 8.9 (s, 1H).

(4)

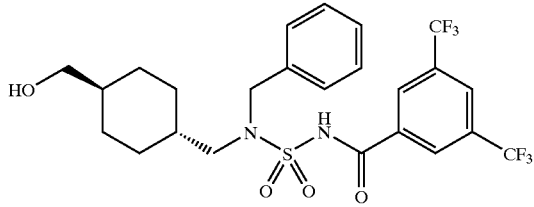

N-benzyl-N'-[3,5-bis(trifluoromethyl)benzoyl]-N-{[4-(hydroxymethyl)cyclohexyl]methyl}sulfamide (4): Silyl ether (3) (49 mg, 73 μmole, 1.0 eq) was dissolved in 3.5 ml of acetic acid/water/tetrahydrofuran in a 4/2/1 v/v ratio and stirred at room temperature overnight. The reaction mixture was diluted with water and ethyl acetate. The water layer was extracted 3× with ethyl acetate and the organic then washed 3× with water. The organic layer was dried over sodium sulfate, filtered and evaporated to give the target compound in 75% yield. Mass spectrum (ES+), calculated M+552.15, observed (M+1) 553.2.

(5)

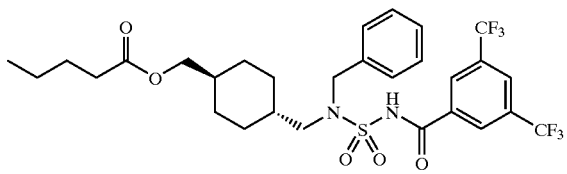

(4-{[benzyl({[3,5-bis(trifluoromethyl)benzoyl]amino}sulfonyl)amino]methyl}cyclohexyl)methyl benzoate (5): Alcohol (6) (80 mg, 140 μmole, 1.0 eq) was suspended in dichloromethane (0.7 ml) and triethylamine (49 μL, 350 μmole 2.5 eq) and benzoyl chloride (20 μL, 168 μmole, 1.2 eq) were added. The reaction was stirred at room temperature overnight, then purified directly by silica gel chromatography to give the title compound. Mass spectrum (ES+), calculated M+656, observed (M+1) 657.

Example 2

(6)

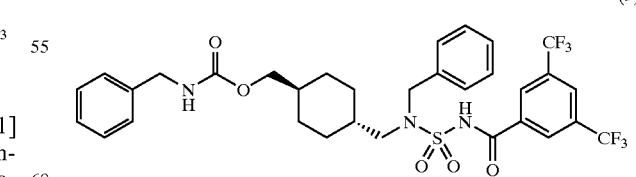

(4-{[benzyl({[3,5-bis(trifluoromethyl)benzoyl]amino}sulfonyl)amino]methyl}cyclohexyl)methyl pentanoate (6): Following procedure to make (5), valeryl chloride was substituted for benzoyl chloride to give the title compound after purification. ¹H NMR (500 MHz, DMSO-d6): δ 8.45 (s, 2H), 8.14 (s, 1H), 7.36 (d, 2H), 7.25 (t, 2H), 7.17 (t, 1H), 4.38 (s, 2H), 3.70 (d, 2H), 3.30 (water), 2.917 (d, 2H), 2.48 (DMSO), 2.22 (t, 2H), 1.62 (m, 2H), 1.52 (m, 2H), 1.45 (m, 2H), 1.37 (m, 1H), 1.26 (m, 1H), 1.22 (m, 2H), 0.82 (t, 3H), 0.63 (m, 4H).

Example 3

(7)

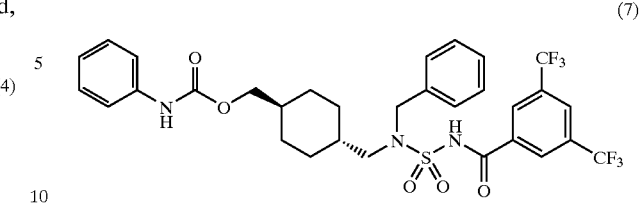

(4-{[benzyl({[3,5-bis(trifluoromethyl)benzoyl]amino}sulfonyl)amino]methyl}cyclohexyl)methyl phenylcarbamate (7): Intermediate (4) (80 mg, 140 μmole, 1.0 eq) was dissolved in acetonitrile (10 mL) and phenyl isocyanate (18 μL, 168 μmole, 1.2 eq) was added. The mixture was refluxed for 24 hours, then diluted with water and extracted repeatedly with dichloromethane. Reconstituted in dichloromethane, filtered off precipitate and purified material isolated from filtrate by RP-HPLC to give title compound. ¹H NMR (400 MHz, MeOH-d4): δ 0–75–9.0 (m, 4H), 1.38–1.60 (m, 2H), 1.68–1.84 (m, 4H), 3.21 (d, 2H, J=8 Hz), 3.86 (d, 2H, J=8 Hz), 4.51 (s, 2H), 7.0 (t, 1H, J=8 Hz) 7.17–7.30 (mult, 5H), 7.33–7.7.45 (mult, 4H), 8.11 (s, 1H), 8.42 (s, 2H).

Example 4

(8)

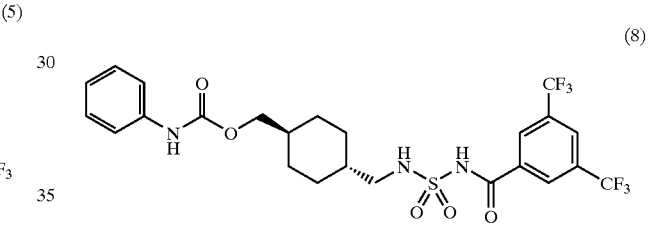

(4-{[({[3,5-bis(trifluoromethyl)benzoyl]amino}sulfonyl)amino]methyl}cyclohexyl)methyl phenylcarbamate (8): 7 (31.5 mg, 47 mmole, 1.0 eq) was dissolved in 4/1 methanol/ethyl acetate (1.25 mL) and 15 mg of 20% palladium hydroxide on carbon (wet) was added. The vessel was evacuated and charged with hydrogen and stirred overnight. The catalyst was fitered over celite and the filtrate evaporated to give the title compound in nearly quantitative yield. ¹H NMR (500 MHz, DMSO-d6): δ 12.23 (br s, 1H), 9.54 (s, 1H), 8.50 (s, 2H), 8.28 (s, 1H), 7.42 (d, 2H), 7.24 (t, 2H), 6.95 (t, 1H), 3.84 (d, 2H), 2.70 (br s, 2H), 1.54-1.38 (m, 2H), 0.88 (m, 4H).

Example 5

(9)

(4-{[benzyl({[3,5-bis(trifluoromethyl)benzoyl]amino}sulfonyl)amino]methyl}cyclohexyl)methyl benzylcarbamate (9): Following procedure to make (5), benzyl isocyanate was substituted for benzoyl chloride to give the title compound after purification. ¹H NMR: (500 MHz, DMSO-d6): δ 12.43 (s, 1H), 8.45 (s, 2H), 8.31 (s, 1H), 7.58

(t, 1H), 7.35 (d, 2H), 7.27 (t, 4H), 7.19 (t, 3H), 4.48 (s, 2H), 4.13 (d, 2H), 3.68 (d, 2H), 3.30 (water), 3.12 (d, 2H), 2.48 (DMSO), 1.62 (m, 4H), 1.45 (m, 1H), 1.37 (m, 1H), 0.63 (m, 4H).

Example 6

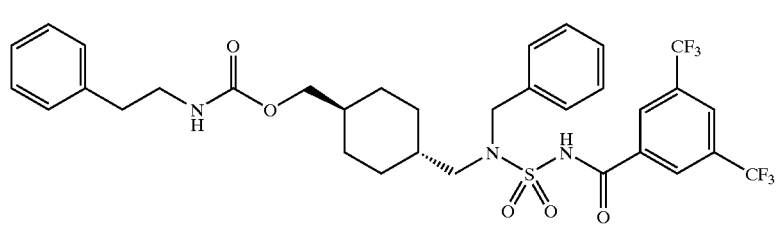

(10)

(4-{[benzyl({[3,5-bis(trifluoromethyl)benzoyl]amino}sulfonyl)amino]methyl}cyclohexyl)methyl 2-phenylethylcarbamate (10): Following procedure to make (9), phenethyl isocyanate was substituted for benzyl isocyanate to give the title compound after purification. ¹H NMR (500 MHz, DMSO-d6): δ 12.43 (s, 1H), 8.45 (s, 2H), 8.10 (s, 1H), 7.37 (d, 2H), 7.27 (t, 3H), 7.16 (m, 3H), 7.07 (t, 2H), 4.34 (s, 2H), 3.61 (d, 2H), 3.14 (m, 2H), 3.30 (water), 2.88 (d, 2H), 2.66 (t, 2H), 2.48 (DMSO), 1.62 (m, 2H), 1.52 (m, 2H), 1.32 (m, 1H), 1.26 (m, 1H), 0.63 (m, 4H).

Example 7

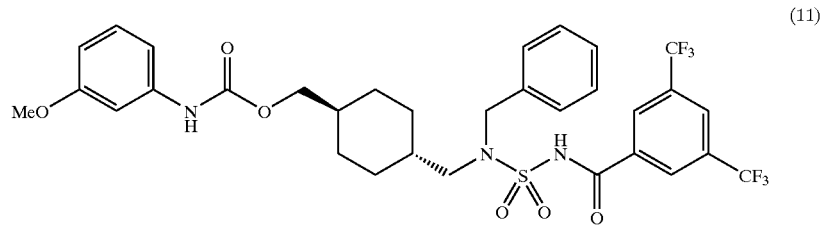

(11)

(4-{[benzyl({[3,5-bis(trifluoromethyl)benzoyl]amino}sulfonyl)amino]methyl}cyclohexyl)methyl 3-methoxyphenylcarbamate (11): Following procedure to make (9), 3-methoxyphenyl isocyanate was substituted for benzyl isocyanate and diisopropylethylamine substituted for triethylamine to give the title compound after purification. ¹H NMR (500 MHz, DMSO-d6): δ 9.50 (s, 1H), 8.45 (s, 2H), 8.10 (s, 1H), 7.38 (d, 2H), 7.24 (t, 2H), 7.14 (m, 3H), 6.96 (d, 1H), 6.52 (d, 1H), 4.35 (s, 2H), 3.75 (d, 2H), 3.68 (s, 3H), 3.30 (water), 2.89 (d, 2H), 2.48 (DMSO), 1.63 (m, 4H), 1.42 (m, 1H), 1.29 (m, 1H), 0.66 (m, 4H).

Example 8

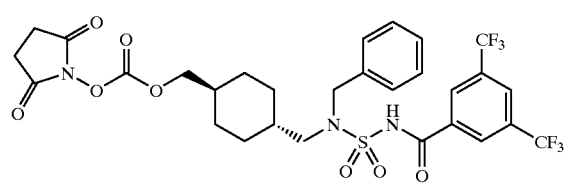

(12)

N-benzyl-N'-[3,5-bis(trifluoromethyl)benzoyl]-N-({4-[({[(2,5-dioxopyrrolidin-1-yl)oxy]carbonyl}oxy)methyl]cyclohexyl}methyl)sulfamide (12): Intermediate (4) (110 mg, 200 μmole, 1.0 eq) was dissolved in acetonitrile, after which triethylamine (84 μL, 600 μmole, 3.0 eq) and disuccinimidyl carbonate (77 mg, 300 μmole, 1.5 eq) were added and the mixture stirred overnight. TLC showed reaction was complete, so it was diluted with ethyl acetate and washed twice with 5% aqueous sodium bicarbonate and once with brine to give the target compound in 97% yield. ¹H NMR (500 MHz, DMSO-d6): δ 8.45 (s, 2H), 8.10 (s, 1H), 7.37 (d, 2H), 7.25 (t, 2H), 7.17 (t, 1H), 4.34 (s, 2H), 4.04 (d, 2H), 3.30 (water), 2.89 (d, 2H), 2.77 (s, 4H), 2.48 (DMSO), 1.65 (m, 2H), 1.54 (m, 2H), 1.51 (m, 1H), 1.26 (m, 1H), 0.65 (m, 4H).

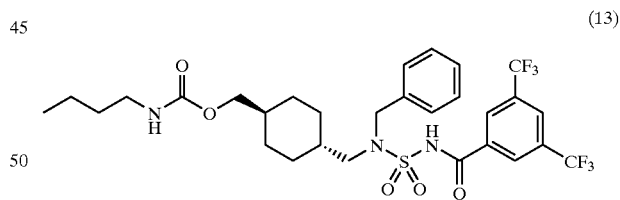

(13)

(4-{[benzyl({[3,5-bis(trifluoromethyl)benzoyl]amino}sulfonyl)amino]methyl}cyclohexyl)methyl butylcarbamate (13): N-butyl amine (6 μL, 60 μmole, 1.2 eq) and triethylamine (10.5 μL, 75 μmole, 1.5 eq) were dissolved in dichloromethane (125 μL), then a solution of (12) (34.7 mg, 50 μmole, 1.0 eq) in dichloromethane (250 μL) was added to the stirring amines. The reaction was stirred overnight, then purified directly by silica gel chromatography to give the title compound in 89% yield. ¹H NMR (500 MHz, DMSO-d6): δ 8.45 (s, 2H), 8.11 (s, 1H), 7.36 (d, 2H), 7.24 (t, 2H), 7.17 (t, 1H), 6.95 (t, 1H), 4.35 (s, 2H), 3.61 (d, 2H), 3.30 (water), 2.89 (d, 4H), 2.48 (DMSO), 1.61 (m, 2H), 1.54 (m, 2H), 1.34–1.19 (m, 6H), 0.82 (t, 3H), 0.61 (m, 4H).

Example 9

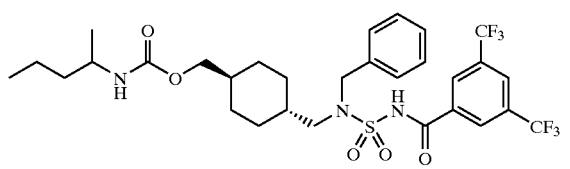
(14)

(4-{[benzyl({[3,5-bis(trifluoromethyl)benzoyl]amino}sulfonyl)amino]methyl}cyclohexyl)methyl 1-methylbutylcarbamate (14): Following the procedure to make (13), 1-methylbutyl amine was substituted for butyl amine to give the title compound after purification. ¹H NMR (500 MHz, DMSO-d6): δ 8.45 (s, 2H), 8.12 (s, 1H), 7.37 (d, 2H), 7.24 (t, 2H), 7.17 (t, 1H), 6.79 (d, 1H), 4.35 (s, 2H), 3.60 (d, 2H), 3.41 (m, 1H), 3.30 (water), 2.89 (d, 2H), 2.48 (DMSO), 1.62 (m, 2H), 1.55 (m, 2H), 1.34–1.19 (m, 6H), 0.96 (d, 3H), 0.80 (t, 3H), 0.62 (m, 4H).

Example 10

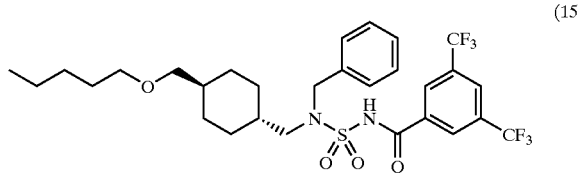
(15)

N-benzyl-N'-[3,5-bis(trifluoromethyl)benzoyl]-N-({4-[(pentyloxy)methyl]cyclohexyl}methyl)sulfamide (15): Intermediate (4) (27.6 mg, 50 µmole, 1.0 eq) was dissolved in dichloromethane (250 µL), after which 2,6-di-t-butyl pyridine (36 µL, 160 µmole, 3.2 eq), silver triflate (38.5 mg, 150 µmole, 3.0 eq) and iodopentane (23 µL, 175 µmole, 3.5 eq) were added. After 45 minutes the reaction mixture was directly purified to give 23 mg of the title compound. ¹H NMR (500 MHz, DMSO-d6): δ 8.45 (s, 2H), 8.15 (s, 1H), 7.36 (d, 2H), 7.24 (t, 2H), 7.17 (t, 1H), 4.39 (s, 2H), 3.30 (water), 3.23 (t, 2H), 3.01 (d, 2H), 2.92 (d, 2H), 2.48 (DMSO), 1.61 (m, 2H), 1.54 (m, 2H), 1.41 (m, 2H), 1.34–1.19 (m, 6H), 0.82 (t, 3H), 0.62 (m, 4H).

Example 11

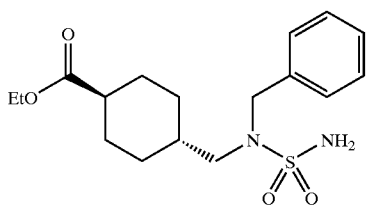
(16)

Ethyl 4-{[(aminosulfonyl)(benzyl)amino]methyl}cyclohexanecarboxylate (16): The hydrochloride salt of trans 4-[benzylamino]methyl]cyclohexane carboxylic acid ethyl ester (CAS 140406-44-6) (275 mg, 0.88 mmole, 1.0 eq) was suspended in 1,2-dimethoxyethane. Triethylamine (139 µL, 1.0 mmole, 1.13 eq) and sulfamide (481 mg, 5.0 mmole, 5.67 eq) were added and the mixture was heated to reflux overnight. DME was evaporated and the crude reconstituted in ethyl acetate, then washed with water. The organic was dried over sodium sulfate, filtered and evaporated. NMR confirms formation of title compound. ¹H NMR (500 MHz, DMSO-d6): δ 7.40–7.20 (m, 5H), 6.79 (s, 2H), 4.18 (s, 2H), 3.99 (m, 2H), 2.81 (d, 2H), 2.08 (m, 1H), 1.74 (m, 2H), 1.61 (m, 2H), 1.25 (m, 1H), 1.12 (t, 3H), 1.02 (dq, 2H), 0.68 (dq, 2H).

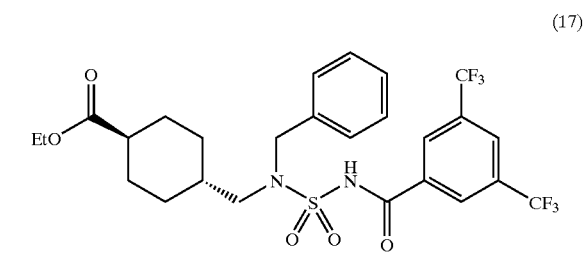
(17)

Ethyl 4-{[benzyl({[3,5-bis(trifluoromethyl)benzoyl]amino}sulfonyl)amino]methyl}cyclohexanecarboxylate (17): A solution of (16) (250 mg, 0.71 mmole, 1.0 eq), dimethyaminopyridine (129 mg, 1.06 mmole, 1.5 eq) and 3,5-bis(trifluoromethyl)benzoyl chloride (141 µL, 0.78 mmole, 1.1 eq) in dichloromethane (5 mL) was stirred overnight. The mixture was diluted further with dichloromethane, washed twice with dilute hydrochloric acid and twice with 5% aqueous sodium bicarbonate. The organic was dried over sodium sulfate, filtered and evaporated and the crude purified by silica gel chromatography to give >85% pure title compound. ¹H NMR (500 MHz, DMSO-d6): δ 8.45 (s, 2H), 8.29 (s, 1H), 7.40–7.20 (m, 5H), 4.46 (s, 2H), 3.98 (m, 2H), 3.09 (d, 2H), 2.09 (m, 1H), 1.74 (m, 2H), 1.61 (m, 2H), 1.25 (m, 1H), 1.11 (t, 3H), 1.02 (dq, 2H), 0.68 (dq, 2H).

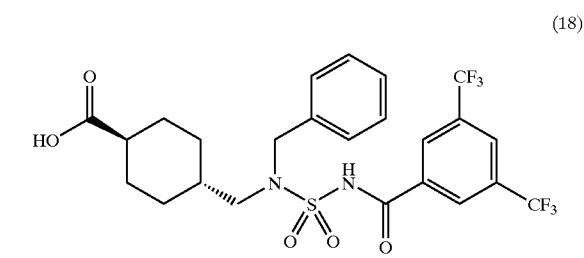
(18)

4-{[benzyl({[3,5-bis(trifluoromethyl)benzoyl]amino}sulfonyl)amino]methyl}cyclohexanecarboxylic acid (18): Intermediate (17) (30 mg, 50 mmole, 1.0 eq) was dissolved in methanol (0.5 mL) and 0.5 N sodium hydroxide was added (0.23 mL, 115 mmole, 2.3 eq). The hydrolysis reaction was heated to 40° C. for 2 hours, at which point hydrolysis was complete. The reaction mixture was diluted with water, acidified with dilute hydrochloric acid and extracted with ethyl acetate. The organic was dried over sodium sulfate, filtered and evaporated to give the title compound in nearly quantitative yield. ¹H NMR (500 MHz, DMSO-d6): δ 12.47 (s, 1H), 11.93 (s, 1H), 8.45 (s, 2H), 8.39 (s, 1H), 7.40–7.20 (m, 5H), 4.52 (s, 2H), 3.21 (d, 2H), 2.09 (m, 1H), 1.76 (m, 2H), 1.61 (m, 2H), 1.33 (m, 1H), 1.02 (m, 2H), 0.80 (m, 2H).

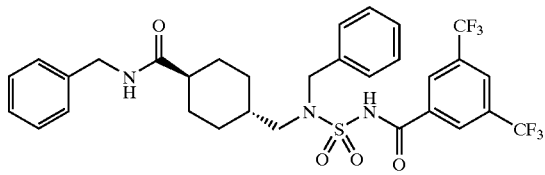

(19)

N-benzyl-4-{[benzyl({[3,5-bis(trifluoromethyl)benzoyl]amino}sulfonyl)amino]methyl}cyclohexane carboxamide (19): Carboxylic acid (18) (27 mg, 48 μmole, 1.0 eq) was dissolved in dichloromethane (250 μL), treated with 1-hydroxybenzotriazole (7.7 mg, 57 μmole, 1.2 eq), 1-(3-dimethylaminopropyl)-3-ethylcarbodiimide hydrochloride (11 mg, 57 μmole, 1.2 eq) and benzylamine (5.7 μL, 52 μmole, 1.1 eq) and stirred for 96 hours. Diluted with dichloromethane, then washed with dilute sodium bicarbonate and dilute hydrochloric acid. The organic layer was dried over sodium sulfate, filtered and evaporated and the crude purified by silica gel chromatography to give the title compound. $^1$H NMR (500 MHz, DMSO-d6): δ 8.45 (s, 2H), 8.16 (s, 1H), 8.13 (t, 1H), 7.40–7.20 (m, 9H), 4.37 (s, 2H), 4.17 (d, 2H), 2.96 (d, 2H), 1.98 (m, 1H), 1.63 (m, 4H), 1.22 (m, 1H), 1.06 (m, 2H), 0.66 (m, 2H).

Example 12

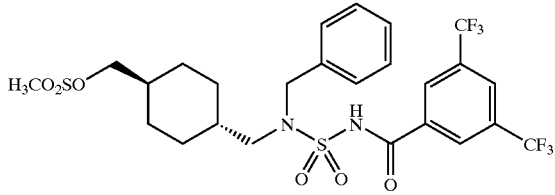

(20)

(4-{[Benzyl({[3,5-bis(trifluoromethyl)benzoyl]amino}sulfonyl)amino]methyl}cyclohexyl)methyl methanesulfonate (20): Intermediate (4) (275 mg, 0.50 mmole, 1.0 eq) was dissolved in dichloromethane (2.5 mL), then treated with triethylamine (175 μL, 1.25 mmole, 2.5 eq) and methanesulfonyl chloride (43 μL, 0.55 mmole, 1.1 eq). The reaction was stirred overnight, then diluted with dichloromethane, washed with 5% aqueous citric acid followed by water, dried over sodium sulfate, filtered and evaporated to give the title compound in 91% yield. $^1$H NMR (500 MHz, DMSO-d6): δ 12.47 (s, 1H), 8.45 (s, 2H), 8.40 (s, 1H), 7.34 (d, 2H), 7.26 (t, 2H), 7.20 (m, 2H), 4.53 (s, 2H), 3.92 (d, 2H), 3.30 (water), 3.22 (d, 2H), 3.10 (s, 3H), 2.48 (DMSO), 1.63 (m, 4H), 1.53 (m, 1H), 1.37 (m, 1H), 0.77 (m, 4H).

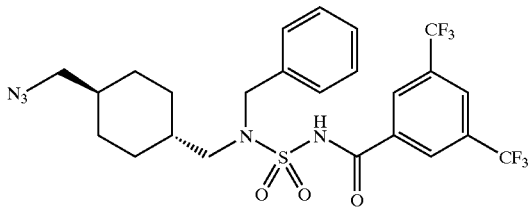

(21)

N-{[4-(azidomethyl)cyclohexyl]methyl}-N-benzyl-N'-[3,5-bis(trifluoromethyl)benzoyl]sulfamide (21): Mesylate (20) (283 mg, 0.45 mmole, 1.0 eq) was dissolved in N,N-dimethylformamide (3 mL) and sodium azide (292 mg, 4.5 mmole, 10.0 eq) was added. CAUTION: SODIUM AZIDE IS EXPLOSIVE. The reaction was heated to 90° C. overnight. The reaction mixture was then diluted with ethyl acetate and washed twice with water and 3× with brine. The organic was dried over sodium sulfate, filtered and evaporated to give the title compound in nearly quantitative yield. $^1$H NMR (500 MHz, DMSO-d6): δ 12.47 (s, 1H), 8.45 (s, 2H), 8.17 (s, 1H), 7.36 (d, 2H), 7.25 (t, 2H), 7.18 (m, 2H), 4.39 (s, 2H), 3.30 (water), 3.08(d, 2H), 2.96 (d, 2H), 2.48 (DMSO), 1.60 (m, 4H), 1.22 (m, 2H), 0.65 (m, 4H).

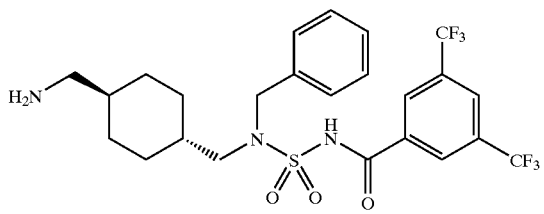

(22)

N-{[4-(aminomethyl)cyclohexyl]methyl}-N-benzyl-N'-[3,5-bis(trifluoromethyl)benzoyl]sulfamide (22): Azide (21) (254 mg, 0.44 mmole, 1.0 eq) was dissolved in methanol (2.2 mL), then the vessel was evacuated and charged with nitrogen. 10% Palladium on carbon (93 mg, 88 μmole, 0.2 eq) was added to the reaction, then the vessel was evacuated and charged with hydrogen gas. Reaction was deemed complete at 4.5 hours. Catalyst was filtered off over a pad of celite and the filtrate was evaporated. The crude product was reconstituted in 1,4-dioxane, then 4N hydrogen chloride in dioxane (180 μL, 720 μmole, 1.6 eq) was added and the solution diluted with ether until the amine hydrochloride salt precipitated out. This was filtered, then the filtrate was evaporated and taken up in 1 ml dioxane. It was diluted again with ether, and a second crop of the amine hydrochloride was obtained. $^1$H NMR (500 MHz, DMSO-d6): δ 12.49 (s, 1H), 8.46 (s, 2H), 8.40 (s, 1H), 7.89 (s, 3H), 7.35 (d, 2H), 7.26 (t, 2H), 7.19 (m, 2H), 4.52 (s, 2H), 3.30 (water), 3.23 (d, 2H), 2.53 (t, 2H), 2.48 (DMSO), 1.65 (m, 4H), 1.38 (m, 2H), 0.71 (m, 4H).

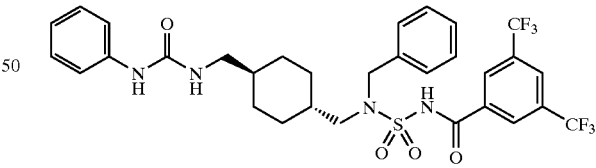

(23)

N-[(4-{[benzyl({[3,5-bis(trifluoromethyl)benzoyl]amino}sulfonyl)amino]methyl}cyclohexyl)methyl]-N'-phenylurea (23): Amine (22) (25.2 mg, 46 μmole, 1.0 eq) was suspended in dichloromethane, then triethylamnine (16 μL, 114 μmole, 2.5 eq) and phenyl isocyanate (6 μL, 55 μmole, 1.2 eq) were added and the reaction stirred overnight. Silica gel chromatography provided the title compound. $^1$H NMR (500 MHz, DMSO-d6): δ 12.46 (s, 1H), 8.45 (s, 2H), 8.27 (s, 1H), 8.23 (s, 1H), 7.36 (d, 2H), 7.32 (d, 2H), 7.25 (t, 2H), 7.18 (m, 4H), 6.84 (t, 1H), 6.05 (t, 1H), 4.43 (s, 2H), 3.30 (water), 3.03 (s, 2H), 2.81 (t, 2H), 2.48 (DMSO), 1.60 (m, 4H), 1.30 (m, 1H), 1.21 (m, 1H), 0.64 (m, 4H).

Example 13

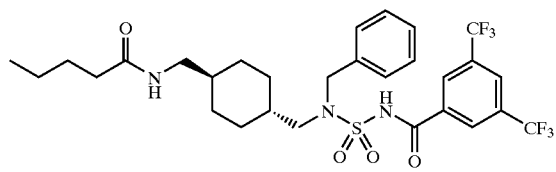

(24)

N-[(4-{[benzyl({[3,5-bis(trifluoromethyl)benzoyl]amino}sulfonyl)amino]methyl}cyclohexyl)methyl]pentanamide (24): Amine (22) (23.5 mg, 40 μmole, 1.0 eq) was suspended in dichloromethane, then triethylamine (16.7 μL, 120 μmole, 3.0 eq) and valeryl chloride (5 μL, 42 μmole, 1.05 eq) were added and the reaction stirred 30 minutes. Silica gel chromatography provided the title compound. $^1$H NMR (500 MHz, DMSO-d6): δ 8.45 (s, 2H), 8.21 (s, 1H), 7.62 (t, 1H), 7.36 (d, 2H), 7.25 (t, 2H), 7.18 (t, 1H), 4.42 (s, 2H), 3.30 (water), 3.00 (s, 2H), 2.74 (t, 2H), 2.48 (DMSO), 1.99 (t, 2H), 1.56 (m, 4H), 1.41 (m, 2H), 1.26 (m, 1H), 1.20 (m, 3H), 0.81 (t, 3H), 0.60 (m, 4H).

Example 14

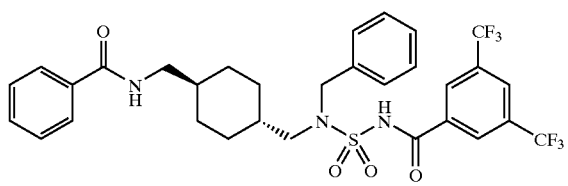

(25)

N-[(4-{[benzyl({[3,5-bis(trifluoromethyl)benzoyl]amino}sulfonyl)amino]methyl}cyclohexyl)methyl]benzamide (25): Amine (22) (23.5mg, 40 μmole, 1.0 eq) was suspended in dichloromethane, then triethylamine (16.7 μL, 120 μmole, 3.0 eq) and benzoyl chloride (4.7 μL, 40 μmole, 1.0 eq) were added and the reaction stirred 30 minutes. Silica gel chromatography provided the title compound. $^1$H NMR (500 MHz, DMSO-d6): δ 8.45 (s, 2H), 8.32 (t, 1H), 8.18 (s, 1H), 7.77 (d, 2H), 7.47 (t, 1H), 7.37 (m, 4H), 7.25 (d, 2H), 7.18 (t, 1H), 4.40 (s, 2H), 3.30 (water), 2.98 (t, 4H), 2.48 (DMSO), 1.61 (m, 4H), 1.36 (m, 1H), 1.28 (m, 1H), 0.62 (m, 4H).

Example 15

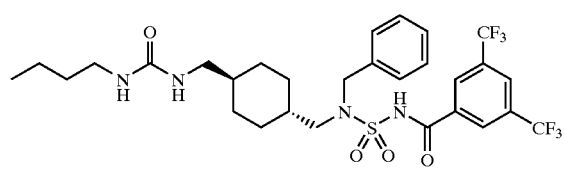

(26)

N-[(4-{[benzyl({[3,5-bis(trifluoromethyl)benzoyl]amino}sulfonyl)amino]methyl}cyclohexyl)methyl]-N'-butylurea (26): Amine (22) (35.3 mg, 60 μmole, 1.0 eq) was suspended in dichloromethane, then triethylamine (25 μL, 180 μmole, 3.0 eq) and disuccinimidyl chloride (19.2 mg, 75 μmole, 1.25 eq) were mixed together and the reaction stirred for 15 minutes. n-Butyl amine (7.4 μL, 75 μmole, 1.25 eq) was then added and the reaction stirred overnight. The mixture was then purified directly by silica gel chromatography to give the title compound. $^1$H NMR (500 MHz, DMSO-d6): δ 8.45 (s, 2H), 8.18 (s, 1H), 7.37 (d, 2H), 7.25 (t, 2H), 7.18 (t, 1H), 5.66 (t, 1H), 4.39 (s, 2H), 3.30 (water), 2.95 (d, 2H), 2.91 (q, 2H), 2.69 (t, 2H), 2.48 (DMSO), 1.56 (m, 4H), 1.25 (m, 5H), 1.10 (m, 1H), 0.83 (t, 3H), 0.57 (m, 4H).

Example 16

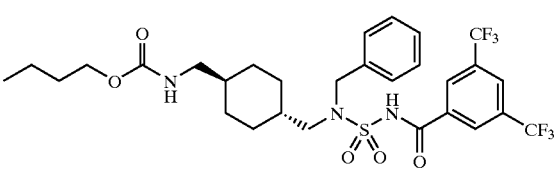

(27)

Butyl (4-{[benzyl({[3,5-bis(trifluoromethyl)benzoyl]amino}sulfonyl)amino]methyl}cyclohexyl)methyl carbamate (27): Amine (22) (60.4 mg, 103 μmole, 1.0 eq) was suspended in dichloromethane, then triethylamine (35.8 μL, 257 μmole, 2.5 eq) and n-butyl chloroformate (13.7 μL, 108 μmole, 1.05 eq) were added and the reaction stirred 4 hours. Silica gel chromatography provided the title compound. $^1$H NMR (500 MHz, DMSO-d6): δ 12.46 (s, 1H), 8.45 (s, 2H), 8.34 (s, 1H), 7.34 (d, 2H), 7.26 (t, 2H), 7.19 (t, 1H), 6.96 (t, 1H), 4.50 (s, 2H), 3.87 (t, 2H), 3.30 (water), 3.13 (d, 2H), 2.70 (t, 2H), 2.48 (DMSO), 1.57 (m, 4H), 1.46 (m, 2H), 1.29 (m, 3H), 1.19 (m, 1H), 0.85 (t, 3H), 0.69 (m, 2H), 0.57 (m, 2H).

Example 17

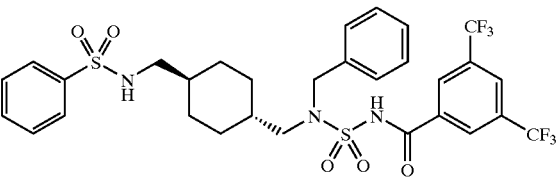

(28)

N-[(4-{[benzyl({[3,5-bis(trifluoromethyl)benzoyl]amino}sulfonyl)amino]methyl}cyclohexyl)methyl]benzenesulfonamide (28): Amine (22) (23.5mg, 40 μmole, 1.0 eq) was suspended in dichloromethane, then triethylamine (16.7 μL, 120 μmole, 3.0 eq) and benzenesulfonylchloride (5.4 μL, 42 μmole, 1.05 eq) were added and the reaction stirred 30 minutes. Silica gel chromatography provided the title compound. $^1$H NMR (500 MHz, DMSO-d6): δ 8.44 (s, 2H), 8.17 (t, 1H), 7.72 (dd, 2H), 7.55 (m, 4H), 7.35 (d, 2H), 7.25 (t, 2H), 7.18 (t, 1H), 4.37 (s, 2H), 3.30 (water), 2.93 (t, 2H), 2.48 (DMSO), 2.44 (t, 2H), 1.61 (m, 4H), 1.21 (m, 1H), 1.11 (m, 1H), 0.51 (m, 4H).

Example 18

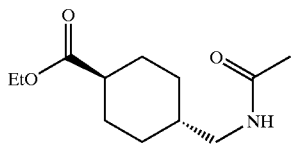

Ethyl 4-[(acetylamino)methyl]cyclohexanecarboxylate (29): trans 4-(Aminomethyl)cyclohexane carboxylic acid ethyl ester (CAS 35879-53-9) (222 mg, 1.0 mmole, 1.0 eq) was dissolved in dichloromethane (5 mL) and triethyl amine (0.35 mL, 2.5 mmole, 2.5 eq) and acetic anhydride (143 μL, 1.50 mmole, 1.5 eq) was added. The reaction was stirred overnight and was complete in 18 hours. The reaction was diluted with dichloromethane and washed twice with dilute aqueous hydrochloric acid. The organic was dried over sodium sulfate, filtered and evaporated to give the title compound in quantitative yield. $^1$H NMR (500 MHz, DMSO-d6): δ 7.76 (s, 1H), 4.01 (q, 2H), 2.85 (t, 2H), 2.17 (m, 1H), 1.86 (m, 2H), 1.77 (s, 3H), 1.69 (m, 2H), 1.24 (m, 3H), 1.13 (t, 3H), 0.88 (m, 2H).

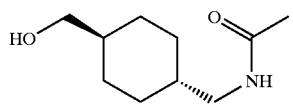

N-{[4-(hydroxymethyl)cyclohexyl]methyl}acetamide (30): Ester (29) (220 mg, 0.97 mmole, 1.0 eq) was dissolved in tetrahydrofuran, then lithium aluminum hydride (81 mg, 2.14 mmole, 2.2 eq) was added and the reaction stirred. This was worked up after 90 minutes by quenching via simultaneous addition of water and 2N sodium hydroxide. The aqueous mixture was extracted with ethyl acetate to give the alcohol title compound in 87% yield. $^1$H NMR (500 MHz, DMSO-d6): δ 7.74 (s, 1H), 4.31 (t, 1H), 3.17 (t, 2H), 2.84 (t, 2H), 1.77 (s, 3H), 1.69 (m, 4H), 1.25 (m, 2H), 0.81 (m, 4H).

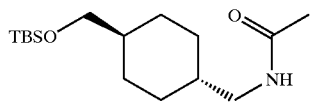

N-{[4-({[tert-butyl(dimethyl)silyl]oxy}methyl)cyclohexyl]methyl}acetamide (31): Primary alcohol (30) was treated with t-butyldimethysilyl chloride and triethylamine in dichloromethane to give title compound in similar fashion to procedure used to make (1). $^1$H NMR (500 MHz, DMSO-d6): δ 7.74 (s, 1H), 3.35 (d, 2H), 2.84 (t, 2H), 1.77 (s, 3H), 1.68 (m, 4H), 1.28 (m, 2H), 0.84 (m, 13H), 0.00 (s, 6H).

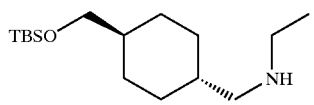

N-{[4-({[tert-butyl(dimethyl)silyl]oxy}methyl)cyclohexyl]methyl}-N-ethylamine (32): Intermediate (31) (50 mg, 168 mmole, 1.0 eq) was dissolved in tetrahydrofuran (0.5 mL) and lithium aluminum hydride (16.4 mg, 432 mmole, 2.6 eq) was added. Heated to reflux for 24 hours at which point reaction was complete. Cooled, quenched with saturated Rochelle's salt, extracted twice with ethyl acetate, dried, filtered and evaporated filtrate to give crude title compound. $^1$H NMR (500 MHz, DMSO-d6): δ 3.35 (d, 2H), 2.45 (m, 2H), 2.29 (d, 2H), 1.72 (m, 4H), 1.28 (m, 2H), 0.96 (t, 3H), 0.84 (m, 13H), 0.00 (s, 6H).

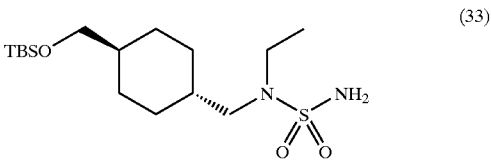

N-{[4-({[tert-butyl(dimethyl)silyl]oxy}methyl)cyclohexyl]methyl}-N-ethylsulfamide (33): Following the procedure to make (16), (32) was treated with sulfamide and DME at reflux overnight to give the title compound. $^1$H NMR (500 MHz, DMSO-d6): δ 6.55 (s, 2H), 3.38 (d, 2H), 3.04 (m, 2H), 2.77 (d, 2H), 1.72 (m, 4H), 1.44 (m, 1H), 1.32 (m, 1H), 1.06 (t, 3H), 0.84 (m, 13H), 0.00 (s, 6H).

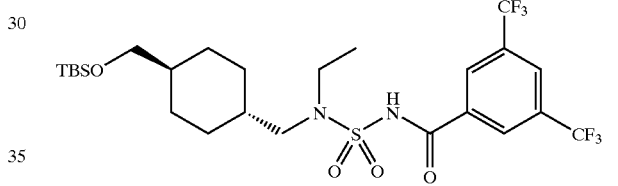

N-{[4-({[tert-butyl(dimethyl)silyl]oxy}methyl)cyclohexyl]methyl}-N-ethylsulfamide (34): Following the procedure to make (17), intermediate (33) was used in place of (16) to give the title compound. $^1$H NMR (500 MHz, DMSO-d6): δ 8.53 (s, 2H), 8.42 (s, 1H), 3.35 (m, 4H), 3.15 (d, 2H), 1.70 (m, 4H), 1.51 (m, 1H), 1.32 (m, 1H), 1.08 (t, 3H), 0.83 (m, 13H), 0.00 (s, 6H).

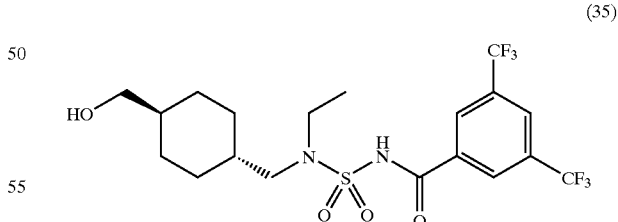

N'-[3,5-bis(trifluoromethyl)benzoyl]-N-ethyl-N-{[4-(hydroxymethyl)cyclohexyl]methyl}sulfamide (35): Following the procedure to make (4), intermediate (34) was substituted for (3) to give the title compound. $^1$H NMR (500 MHz, DMSO-d6): δ 8.43 (s, 2H), 8.09 (s, 1H), 4.28 (t, 1H), 3.15 (m, 4H), 2.91 (d, 2H), 1.74 (m, 4H), 1.43 (m, 1H), 1.24 (m, 1H), 1.02 (t, 3H), 0.78 (m, 4H).

(36)

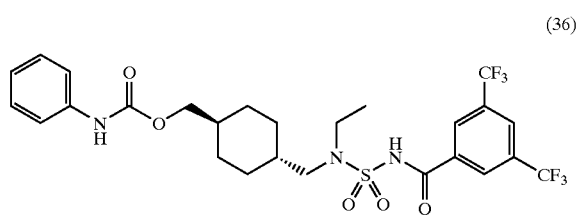

(4-{[({[3,5-bis(trifluoromethyl)benzoyl]amino}sulfonyl)(ethyl)amino]methyl}cyclohexyl)methyl phenylcarbamate (36): Alcohol (35) (11.6 mg, 24 mmole, 1.0 eq) was dissolved in dichloromethane followed by the addition of triethylamine (10 mL, 72 mmole, 3.0 eq) and phenyl isocyanate (2.8 mL, 26 mmole, 1.05 eq). Added additional triethylamine and phenylisocyanate to drive reaction to completion. Purified by silica gel chromatography to provide the title compound. ¹H NMR (500 MHz, DMSO-d6): δ 12.39 (s, 1H), 9.55 (s, 1H), 8.54 (s, 2H), 8.39 (s, 1H), 7.43 (s, 2H), 7.24 (t, 2H), 6.95 (t, 1H), 3.88 (d, 2H), 3.35 (q, 2H), 3.19 (d, 2H), 1.77 (m, 4H), 1.57 (m, 2H), 1.09 (t, 3H), 0.92 (m, 4H).

Example 19

(37)

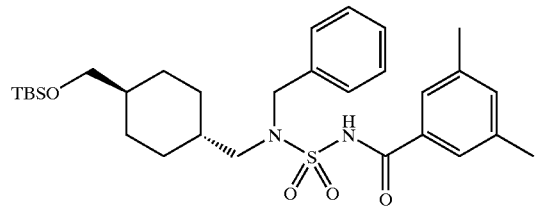

N-benzyl-N-{[4-({[tert-butyl(dimethyl)silyl]oxy}methyl)cyclohexyl]methyl}-N'-(3,5-dimethylbenzoyl)sulfamide (37): 3,5-Dimethylbenzoic acid (1.50 g, 10.0 mmole, 1.0 eq) was suspended in 5 mL dichloromethane and heated to reflux, after which a solution of chlorosulfonyl isocyanate (0.87 mL, 10.0 mmole, 1.0 eq) in 2 mL dichloromethane was added. Reaction mixture became clear, and remained so after 40 minutes of reflux. Cooled to room temperature, added hexanes and began to evaporate when solid precipitated out. Recovered filtered solid. 23 mg, 92 μmole, 1.0 eq of this material was added to a mixture of intermediate (2) (34 mg, 92 μmole, 1.0 eq) and triethylamine (39 μL, 277 μmole, 3.0 eq) in dichloromethane (0.5 mL). Reaction was complete at 2 hours, at which point it was purified directly by silica gel chromatography to give the title compound in 86% yield. ¹H NMR (500 MHz, DMSO-d6): δ 11.84 (s, 1H), 7.49 (s, 2H), 7.31 (m, 6H), 4.52 (s, 2H), 3.28 (d, 2H), 3.09 (d, 2H), 2.30 (s, 6H), 1.58 (m, 4H), 1.31 (m, 1H), 1.22 (m, 1H), 0.82 (s, 9H), 0.66 (m, 4H), 0.04 (s, 6H).

(38)

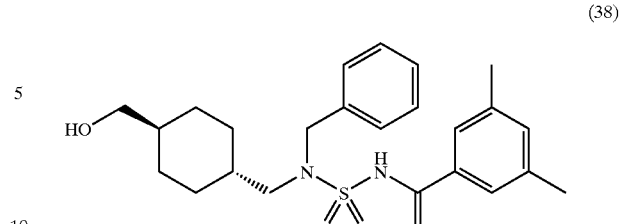

N-benzyl-N'-(3,5-dimethylbenzoyl)-N-{[4-(hydroxymethyl)cyclohexyl]methyl}sulfamide (38): Intermediate (37) was treated as (3) was treated in the synthesis of (4) to give the title alcohol in quantitative yield. ¹H NMR (500 MHz, DMSO-d6): δ 11.85 (s, 1H), 7.50 (s, 2H), 7.31 (m, 6H), 4.52 (s, 2H), 4.27 (t, 1H), 3.10 (m, 4H), 2.32 (s, 6H), 1.59 (m, 4H), 1.31 (m, 1H), 1.22 (m, 1H), 0.66 (m, 4H).

(39)

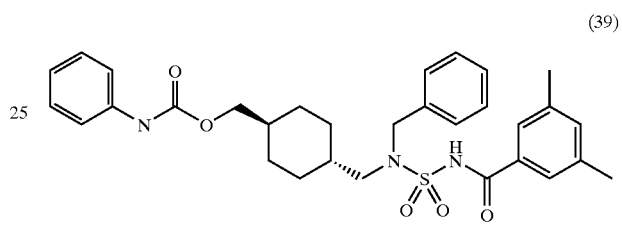

{4-[(benzyl{[(3,5-dimethylbenzoyl)amino]sulfonyl}amino)methyl]cyclohexyl}methyl phenylcarbamate (39): Alcohol (38) (34.6 mg, 78 mmole, 1.0 eq) in 0.5 mL dichloromethane was treated with triethylamine (38 mL, 272 mmole, 3.5 eq) and phenyl isocyanate (17 mL, 156 mmole, 2.0 eq) to give the title compound after preparative TLC. ¹H NMR (500 MHz, DMSO-d6): δ 11.85 (s, 1H), 9.52 (s, 1H), 7.50 (s, 2H), 7.41 (d, 2H), 7.36 (d, 2H), 7.30 (t, 2H), 7.24 (t, 3H), 7.19 (s, 1H), 6.95 (t, 1H), 4.48 (s, 2H), 3.800 (d, 2H), 3.07 (d, 2H), 2.32 (s, 6H), 1.64 (m, 4H), 1.47 (m, 1H), 1.34 (m, 1H), 0.73 (m, 4H).

Example 20

(40)

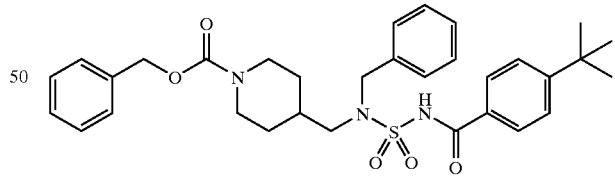

4-(benzyl-{[(4-t-butylbenzoyl)amino]sulfonyl}aminomethyl)-1-piperidinecarboxylic acid phenylmethyl ester (40): 4-[[benzylamino]methyl]-1-piperidinecarboxylic acid phenylmethyl ester (CAS 195314–74–0) was converted to the title compound following the procedures described to prepare sulfamide (16) and acyl sulfamide (17).

¹H NMR (CDCl3): δ 8.35 (s, 1H), 7.66 (d, J=8 Hz, 2H), 7.50 (d, J=8 Hz, 2H), 7.35 (m, 10H), 5.08 (s, 2H), 4.57 (bs, 2H), 4.08 (m, 2H), 3.36 (m, 2H), 2.53 (m, 2H), 1.55 (m, 3H), 1.34 (s, 9H), 1.03 (m, 2H).

What is claimed is:

1. A compound having the formula I:

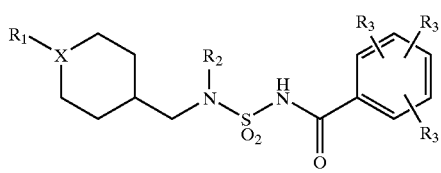

or a pharmaceutically acceptable salt thereof, wherein

X is selected from CH and N;

$R_1$ is $-(CH_2)_a(Y_1)_b(Z)_c(Y_2)_d R_4$;

a, b, c, and d are each independently 0 or 1, with the proviso that if c is 0, then b and d are not both 1;

$Y_1$ and $Y_2$ are each independently O or NH;

Z is selected from C(O) and S(O)$_2$;

$R_2$ is selected from H, $C_{1-6}$ alkyl, $C_{2-6}$ alkenyl, $C_{2-6}$ alkynyl, $C_{3-10}$ Cycloalkyl, $C_{6-10}$ Aryl, Heteroaryl, and Heterocycle, and $R_2$ is optionally substituted with 1–5 groups $R_3$;

Each $R_3$ is independently selected from H, halogen, $C_{1-6}$ alkyl, $C_{2-6}$ alkenyl, $C_{2-6}$ alkynyl, $C_{6-10}$ Aryl, —O$C_{1-6}$ alkyl, —O$C_{2-6}$ alkenyl, —O$C_{2-6}$ alkynyl, —O$C_{6-10}$ Aryl, $C_{3-6}$ Cycloalkyl, Heteroaryl, Heterocycle, CN, NO$_2$, S(O)$_m$R$_4$, SO$_2$NHR$_4$, SO$_2$NR$_4$R$_4$, CO$_2$H, and CONHR$_4$, wherein each alkyl, alkenyl, alkynyl, Aryl, -Oalkyl, -Oalkenyl, -Oalkynyl, -Oaryl, Cycloalkyl, Heteroaryl, and Heterocycle is optionally substituted with 1–5 substituents independently selected from halogen, —OCF$_3$, —OCH$_3$, CF$_3$ and CH$_3$;

Each $R_4$ is independently selected from the group consisting of H, $C_{1-10}$ alkyl, $C_{3-10}$ Cycloalkyl, $C_{2-10}$ alkenyl, $C_{2-10}$ alkynyl, $C_{6-10}$ Aryl, Heterocycle, and Heteroaryl, wherein $R_4$ is optionally substituted with 1–3 groups $R_5$;

Each $R_5$ is independently selected from halogen, $C_{1-6}$ alkyl, $C_{6-10}$ Aryl, —O$C_{16}$ alkyl, —O$C_{2-6}$ alkenyl, —O$C_{2-6}$ alkynyl, —O$C_{6-10}$ Aryl, $C_{3-6}$ Cycloalkyl, CN, NO$_2$, CO$_2$H, CO$_2$C$_1$-C$_6$alkyl and CONH$_2$, wherein each alkyl, Aryl, -Oalkyl, -Oalkenyl, -Oalkynyl, -Oaryl, Cycloalkyl and CO$_2$alkyl is optionally substituted with 1–5 substituents independently selected from halogen, —OCF$_3$, —OCH$_3$, CF$_3$ and CH$_3$;

m is 0, 1 or 2;

Each alkyl, alkenyl and alkynyl group may be linear or branched;

Cycloalkyl is a saturated or partly saturated monocyclic or bicyclic carbocyclic ring system;

Aryl is a monocyclic or bicyclic carbocyclic aromatic ring system;

Heterocycle is a fully saturated or partially saturated monocyclic or bicyclic ring system comprising at least one heteroatom selected from N, S and O in the ring and comprising 4 to 11 atoms in the ring; and Heteroaryl is a monocyclic or bicyclic aromatic ring system comprising at least one ring heteroatom selected from N, O and S and comprising 4–11 atoms in the ring or rings.

2. A compound having formula I as recited in claim 1, wherein X is CH.

3. A compound having formula I as recited in claim 2, wherein $R_1$ is selected from the group consisting of CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, CH$_2$NHS(O)$_2$R$_4$, CONHR$_4$, S(O)$_2$NHR$_4$, OCONHR$_4$, NHCOOR$_4$, NHCONHR$_4$, NHS(O)$_2$NHR$_4$, NHCOR$_4$, and NHS(O)$_2$R$_4$.

4. A compound having Formula I as recited in claim 2, wherein R1 is selected from the group consisting of CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, and CH$_2$NHS(O)$_2$R$_4$.

5. A compound having Formula I as recited in claim 1, wherein X is N.

6. A compound having Formula I as recited in claim 5, wherein $R_1$ is selected from the group consisting of CONHR$_4$, COOR$_4$, COR$_4$, S(O)$_2$R$_4$, and S(O)$_2$NHR$_4$.

7. A compound having Formula I as recited in claim 1, wherein $R_2$ is selected from $C_{1-6}$ alkyl, CH$_2$C$_{3-10}$ Cycloalkyl and CH$_2$C$_{6-10}$ Aryl, wherein $R_2$ is optionally substituted with 1–3 halogens, and Cycloalkyl and Aryl are optionally substituted with 1–3 groups $R_3$.

8. A compound having Formula I as recited in claim 1, wherein $R_2$ is CH$_2$phenyl, where phenyl is optionally substituted with 1–3 groups $R_3$.

9. A compound having Formula I as recited in claim 1, wherein each $R_3$ is independently selected from the group consisting of H, halogen, $C_{1-6}$ alkyl, and —O$C_{1-6}$ alkyl, wherein alkyl and -Oalkyl are optionally substituted with 1–5 fluorine atoms.

10. A compound having Formula I as recited in claim 1, wherein each $R_4$ is independently selected from the group consisting of H, $C_{1-6}$ alkyl, $C_{3-6}$ Cycloalkyl, phenyl, and Heteroaryl, wherein Cycloalkyl is a monocyclic carbocyclic ring and Heteroaryl is a monocyclic 5 or 6-membered aromatic ring having at least one heteroatom selected from O, S and N in the ring, and $R_4$ is optionally substituted with 1–3 $R_5$.

11. A compound having Formula I as recited in claim 1, wherein $R_4$ is selected from the group consisting of H, phenyl and $C_{1-6}$alkyl, wherein phenyl is optionally substituted with 1–3 groups independently selected from halogen, CH$_3$, CF$_3$, —OCH$_3$ and —OCF$_3$, and alkyl is optionally substituted with 1–3 halogens and/or one phenyl, which is optionally substituted with 1–3 groups independently selected from halogen, CH$_3$, CF$_3$, —OCH$_3$ and —OCF$_3$.

12. A compound having Formula I as recited in claim 1, wherein:

X is selected from CH and N, wherein when X is CH, $R_1$ is selected from the group consisting of CH$_2$OCONHR$_4$, CH$_2$OCOOR$_4$, CH$_2$OCOR$_4$, CH$_2$OR$_4$, CH$_2$NHCOOR$_4$, CH$_2$NHCONHR$_4$, CH$_2$NHCOR$_4$, CH$_2$NHS(O)$_2$NHR$_4$, and CH$_2$NHS(O)$_2$R$_4$, and when X is N, $R_1$ is selected from the group consisting of CONHR$_4$, COOR$_4$, COR$_4$, S(O)$_2$R$_4$, and S(O)$_2$NHR$_4$;

$R_2$ is benzyl or $C_{1-6}$ alkyl, and $R_2$ is optionally substituted with 1–3 $R_3$;

$R_3$ is selected from the group consisting of H, halogen, $C_{1-6}$alkyl, —OCH$_3$ and —OCF$_3$, wherein alkyl is optionally substituted with 1–3 halogens; and Each $R_4$ is independently selected from the group consisting of H, phenyl and $C_{1-6}$alkyl, wherein phenyl is optionally substituted with 1–3 groups independently selected from halogen, CH$_3$, CF$_3$, —OCH$_3$ and —OCF$_3$, and alkyl is optionally substituted with 1–3 halogens and optionally 1 phenyl, which is optionally substituted with 1–3 groups independently selected from halogen, CH$_3$, CF$_3$, —OCH$_3$ and —OCF$_3$.

13. A compound having Formula I as recited in claim 12, wherein $R_2$ is benzyl.
14. A compound represented by a structure shown below, or a pharmaceutically acceptable salt thereof:
| STRUCTURE |
|---|
| 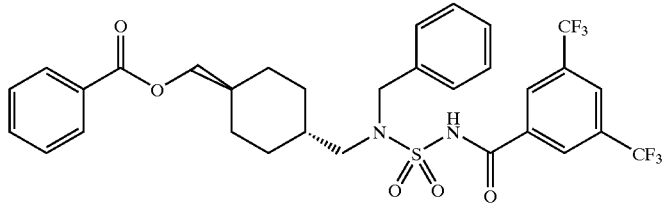 |
| 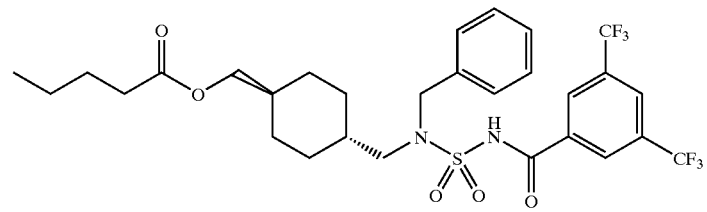 |
| 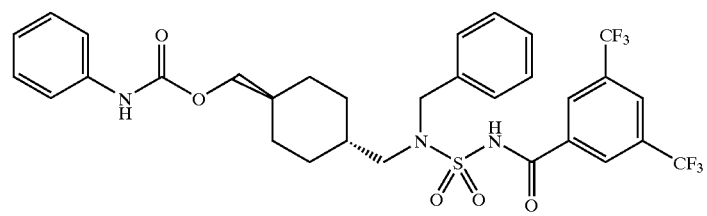 |
| 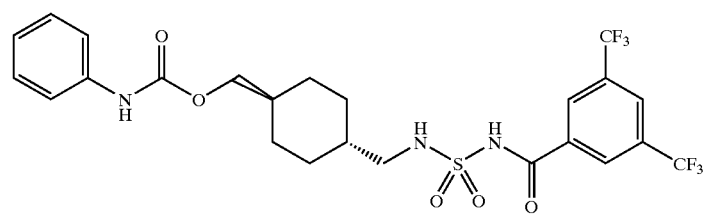 |
| 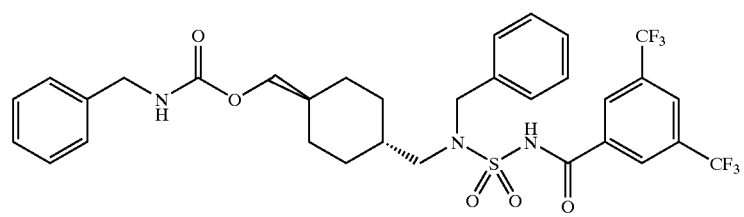 |
| 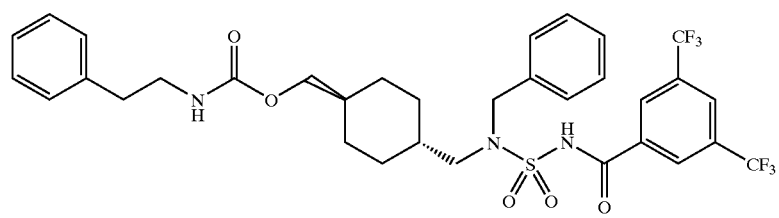 |

-continued
STRUCTURE
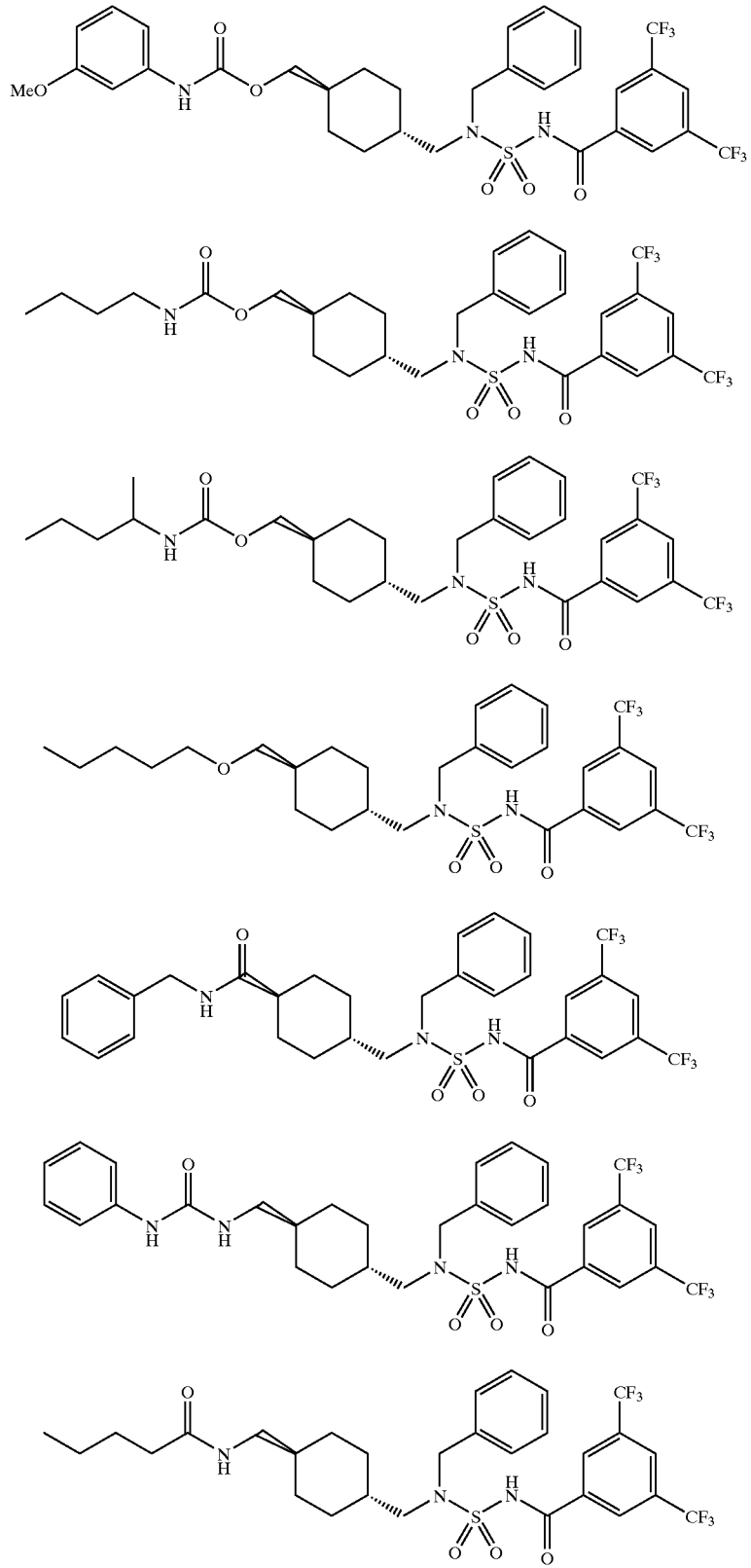

-continued
STRUCTURE
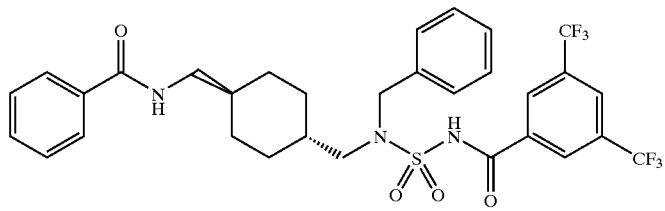
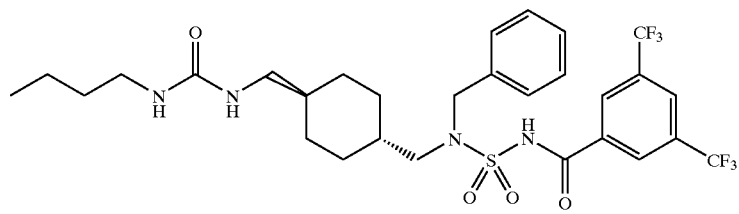
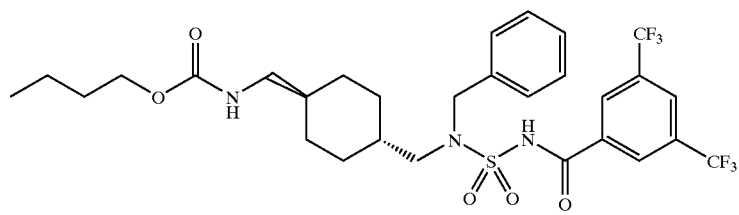
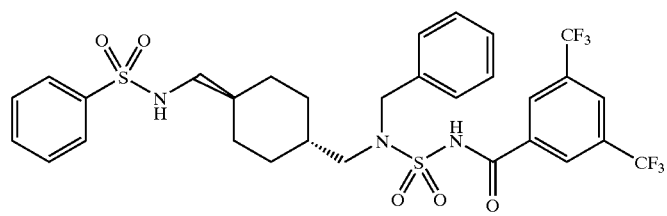
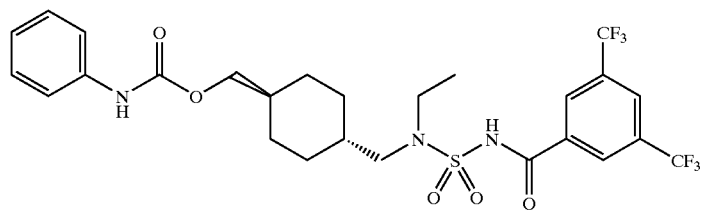
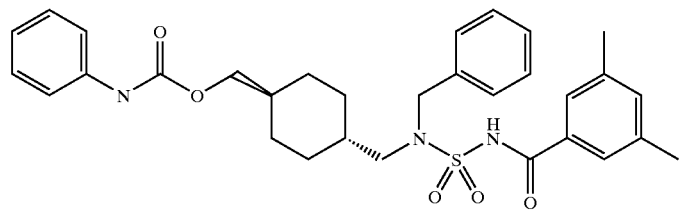
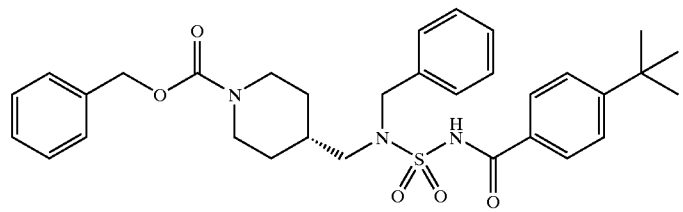

15. A compound named below, or a pharmaceutically acceptable salt thereof:
1. (4-{[benzyl({[3,5-bis(trifluoromethyl)benzoyl]amino}sulfonyl)amino]methyl}-cyclohexyl)methyl benzoate;
2. (4-{[benzyl({[3,5-bis(trifluoromethyl)benzoyl]amino}sulfonyl)amino]methyl}-cyclohexyl)methyl pentanoate;
3. (4-{[benzyl({[3,5-bis(trifluoromethyl)benzoyl]amino}sulfonyl)amino]methyl}-cyclohexyl)methyl phenylcarbamate;
4. (4-{[({[3,5-bis(trifluoromethyl)benzoyl]amino}sulfonyl)amino]methyl}cyclohexyl)methyl phenylcarbamate;
5. (4-{[benzyl({[3,5-bis(trifluoromethyl)benzoyl]amino}sulfonyl)amino]methyl}-cyclohexyl)methyl benzylcarbamate;
6. (4-{[benzyl({[3,5-bis(trifluoromethyl)benzoyl]amino}sulfonyl)amino]methyl}-cyclohexyl)methyl 2-phenylethylcarbamate;
7. (4-{[benzyl({[3,5-bis(trifluoromethyl)benzoyl]amino}sulfonyl)amino]methyl}-cyclohexyl)methyl 3-methoxyphenylcarbamate;
8. (4-{[benzyl({[3,5-bis(trifluoromethyl)benzoyl]amino}sulfonyl)amino]methyl}-cyclohexyl)methyl butylcarbamate;
9. (4-{[benzyl({[3,5-bis(trifluoromethyl)benzoyl]amino}sulfonyl)amino]methyl}-cyclohexyl)methyl 1-methylbutylcarbamate;
10. N-benzyl-N'-[3,5-bis(trifluoromethyl)benzoyl]-N-({4-[(pentyloxy)methyl]cyclohexyl}methyl)sulfamide;
11. N-benzyl-4-{[benzyl({[3,5-bis(trifluoromethyl)benzoyl]amino}sulfonyl)amino]methyl}-cyclohexane carboxamide;
12. N-[(4-{[benzyl({[3,5-bis(trifluoromethyl)benzoyl]amino}sulfonyl)amino]methyl}-cyclohexyl)methyl]-N'-phenylurea;
13. N-[(4-{[benzyl({[3,5-bis(trifluoromethyl)benzoyl]amino}sulfonyl)amino]methyl}-cyclohexyl)methyl] pentanamide;
14. N-[(4-{[benzyl({[3,5-bis(trifluoromethyl)benzoyl]amino}sulfonyl)amino]methyl}-cyclohexyl)methyl] benzamide;
15. N-[(4-{[benzyl({[3,5-bis(trifluoromethyl)benzoyl]amino}sulfonyl)amino]methyl}-cyclohexyl)methyl]-N'-butylurea;
16. Butyl (4-{[benzyl({[3,5-bis(trifluoromethyl)benzoyl]amino}sulfonyl)amino]methyl}-cyclohexyl)methyl carbamate;
17. N-[(4-{[benzyl({[3,5-bis(trifluoromethyl)benzoyl]amino}sulfonyl)amino]methyl}-cyclohexyl)methyl] benzenesulfonamide;
18. (4-{[({[3,5-bis(trifluoromethyl)benzoyl]amino}sulfonyl)(ethyl)amino]methyl}-cyclohexyl) methyl phenylcarbamate;
19. {4-[(benzyl{[(3,5-dimethylbenzoyl)amino]sulfonyl}amino)methyl]cyclohexyl}methyl -phenylcarbamate; and
20. 4-(benzyl-{[(4-t-butylbenzoyl)amino]sulfonyl}aminomethyl)-1-piperidinecarboxylic acid phenylmethyl ester.

16. A pharmaceutical composition comprising a compound of claim 1 and a pharmaceutically acceptable carrier.

17. A method for treating or controlling obesity in a mammalian patient in need of such treatment which comprises administering to said patient a therapeutically effective amount of a compound of claim 1.

18. A method for treating or controlling non-insulin dependent (Type 2) diabetes mellitus in a mammalian patient in need of such treatment which comprises administering to said patient a therapeutically effective amount of a compound of claim 1.

19. A method for treating or controlling hyperglycemia in a mammalian patient in need of such treatment which comprises administering to said patient a therapeutically effective amount of a compound of claim 1.

20. A method for treating or controlling lipid disorders, hyperlipidemia, or low HDL in a mammalian patient in need of such treatment which comprises administering to said patient a therapeutically effective amount of a compound of claim 1.

21. A method for treating or controlling hypercholesterolemia in a mammalian patient in need of such treatment which comprises administering to said patient a therapeutically effective amount of a compound of claim 1.

22. A method for treating or controlling hypertriglyceridemia in a mammalian patient in need of such treatment which comprises administering to said patient a therapeutically effective amount of a compound of claim 1.

23. A method for treating or controlling dyslipidemia and/or low HDL cholesterol in a mammalian patient in need of such treatment which comprises administering to said patient a therapeutically effective amount of a compound of claim 1.

24. A method for treating or controlling atherosclerosis in a mammalian patient in need of such treatment which comprises administering to said patient a therapeutically effective amount of a compound of claim 1.

25. A method of treating or controlling one or more diseases, disorders, or conditions selected from the group consisting of (1) obesity, (2) non-insulin dependent diabetes mellitus (NIDDM), (3) hyperglycemia, (4) low glucose tolerance, (5) insulin resistance, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) neoplastic conditions, (23) adipose cell tumors, (24) adipose cell carcinomas, such as liposarcoma, (25) prostate cancer and other cancers, including gastric, breast, bladder and colon cancers, (26) angiogenesis, (27) Alzheimer's disease, (28) psoriasis, (29) acne vulgaris, (30) other skin diseases and dermatological conditions modulated by PPAR, (31) high blood pressure, (32) Syndrome X, (33) ovarian hyperandrogenism (polycystic ovarian syndrome), and other disorders where insulin resistance is a component, said method comprising the administration of an effective amount of a compound of claim 1.

26. A method for the treatment or controlling one or more conditions selected from inflammatory conditions, inflammatory bowel disease, Crohn's disease, and ulcerative colitis, which method comprises administering to a mammalian patient in need of such treatment a therapeutically effective amount of a compound of claim 1.

* * * * *